(12) United States Patent
Shih et al.

(10) Patent No.: US 8,673,272 B2
(45) Date of Patent: Mar. 18, 2014

(54) ULTRAVIOLET-ABSORBING COMPOUNDS

(75) Inventors: Jenn S. Shih, Paramus, NJ (US); Osama M. Musa, Hillsborough, NJ (US)

(73) Assignee: ISP Investments Inc., Wilmington, DE (US)

( * ) Notice: Subject to any disclaimer, the term of this patent is extended or adjusted under 35 U.S.C. 154(b) by 344 days.

(21) Appl. No.: 12/841,716

(22) Filed: Jul. 22, 2010

(65) Prior Publication Data

US 2011/0020251 A1    Jan. 27, 2011

Related U.S. Application Data

(60) Provisional application No. 61/228,668, filed on Jul. 27, 2009.

(51) Int. Cl.
*A61K 8/44* (2006.01)
*C07C 229/34* (2006.01)

(52) U.S. Cl.
USPC ............................................. 424/59; 560/36

(58) Field of Classification Search
USPC ............................................. 424/59; 560/36
See application file for complete search history.

(56) References Cited

U.S. PATENT DOCUMENTS 2,961,347 A    11/1957  Floyd (Continued)

FOREIGN PATENT DOCUMENTS

| WO | WO 00/78864 A2 | 12/2000 |
| WO | PCT/EP2007/051697 | 2/2007 |
| WO | WO 2008/066849 | 6/2008 |

OTHER PUBLICATIONS

Shams et al., Synthesis of new disperse azo dyes based on oxopyridine core, 2008, Pigment & Resin Technology, 37 (5), 299-307.*
Billingham, N.C., *Molar Mass Measurements in Polymer Science*, Halsted Press, 1979.
Billmeyer, F., *Textbook of Polymer Science*, Wiley Interscience, 1984.
Dixon, K.W., "Decomposition Rate of Organic Free Radical Polymerization," section II in *Polymer Handbook*, vol. 1, 4$^{th}$ edition, Wiley-Interscience, 1999.
Grob, R.L., and Barry, E.F., *Modern Practice of Gas Chromatography*, third edition, John Wiley & Sons, 1995.

(Continued)

*Primary Examiner* — Kristin Vajda
(74) *Attorney, Agent, or Firm* — William J. Davis; Thompson Hine LLP

(57) ABSTRACT

Disclosed are novel ultraviolet-absorbing compounds produced by two embodiments. By a first embodiment, the ultraviolet-absorbing compound is derived from at a first reactant being a UV absorber comprising a carbon-nitrogen triple bond and a second reactant having amine functionality. By a second embodiment, the ultraviolet-absorbing compound is derived from a first reactant being a UV absorber comprising amine functionality and a second reactant comprising a carbon-nitrogen triple bond. In both embodiments of the invention, the second reactant may be a small molecule, a monomer, a macromolecule, a biomolecule, or a polymer.

The invention's ultraviolet-absorbing compounds are directed toward formulations and applications that serve to protect against UV radiation in any art. Exemplary uses of the ultraviolet-absorbing compounds are in adhesive, agriculture, cleaning/polishing, coating, containers, encapsulation, fragrances, imaging, hoses/tubing, household/industrial/institutional, medical, membrane, molded parts, oilfield, packaging, personal care, personal protective equipment, pharmaceutical, printing, veterinary, and wood-care applications. Highly preferred uses of the ultraviolet-absorbing compounds are in personal care and performance chemicals.

wherein R=

16 Claims, No Drawings

(56) References Cited

U.S. PATENT DOCUMENTS

| | | |
|---|---|---|
| 3,227,615 A | 1/1966 | Korden |
| 3,589,578 A | 6/1971 | Kamphausen |
| 4,031,307 A | 6/1977 | DeMartino et al. |
| 4,077,441 A | 3/1978 | Rosen et al. |
| 4,104,248 A | 8/1978 | Cantatore |
| 4,131,576 A | 12/1978 | Iovine et al. |
| 4,698,381 A | 10/1987 | Minagawa et al. |
| 4,850,517 A | 7/1989 | Ter Stege |
| 4,882,412 A | 11/1989 | Weaver et al. |
| 5,057,588 A | 10/1991 | East et al. |
| 5,270,379 A | 12/1993 | McAndrew et al. |
| 5,373,052 A | 12/1994 | Fukuda et al. |
| 5,496,545 A | 3/1996 | Holmes-Farley et al. |
| 5,624,963 A | 4/1997 | Mandeville et al. |
| 5,667,775 A | 9/1997 | Holmes-Farley et al. |
| 5,679,717 A | 10/1997 | Mandeville et al. |
| 5,693,675 A | 12/1997 | Mandeville et al. |
| 5,703,188 A | 12/1997 | Mandeville et al. |
| 6,001,952 A | 12/1999 | Carman et al. |
| 6,008,316 A | 12/1999 | Foster et al. |
| 6,059,870 A | 5/2000 | Taylor et al. |
| 6,150,494 A | 11/2000 | Wang et al. |
| 6,492,455 B1 | 12/2002 | Nadolsky |
| 7,084,189 B2 | 8/2006 | Banning et al. |
| 7,435,291 B2 | 10/2008 | Moffatt et al. |
| 2009/0012241 A1 | 1/2009 | Kozlowski et al. |

OTHER PUBLICATIONS

Hanson K.M.; Gratton E.; Bardeen C.J. (2006). "Sunscreen enhancement of UV-induced reactive oxygen species in the skin," *Free Radical Biology and Medicine*, 41, 8, 1205-1212.

"The Jeffamine® Polyetheramines," sales brochure of Huntsman Corporation, May 2007.

Kirk-Othmer Encyclopedia of Chemical Technology, third edition, vol. 20, John Wiley & Sons, New York, 1982.

Morrison, R.T. and Boyd, R.N., *Organic Chemistry sixth edition*, Prentice-Hall International, 1992.

Saxena, A., et al., "Synthesis and properties of polyether nitrile copolymers with pendant methyl groups," (2003) *Eur Poly J*, 39, 57-61.

Schroder, E., et al., *Polymer Characterization*, Hanser Publishers, 1989.

Silverstein, R.M., et al., *Spectrometric Identification of Organic Compounds*, John Wiley & Sons, 1981.

Yoder, C.H. and Schaeffer Jr., C.D., *Introduction to Multinuclear NMR*, the Benjamin/Cummings Publishing Company, Inc., 1987.

\* cited by examiner

ULTRAVIOLET-ABSORBING COMPOUNDS

BACKGROUND OF THE INVENTION

1. Field of the Invention

The invention discloses a new class of compounds that absorbs ultraviolet (UV) radiation, being produced by two embodiments. By a first embodiment, the ultraviolet-absorbing compound is derived from at least one first reactant being a UV absorber having a carbon-nitrogen triple bond and at least one second reactant having amine functionality. Alternatively, by a second embodiment the ultraviolet-absorbing compound is derived from at least one first reactant being a UV absorber with amine functionality and at least one second reactant comprising a carbon-nitrogen triple bond. In both embodiments of the invention, the second reactant may be a small molecule, a monomer, a macromolecule, a biomolecule, or a polymer.

The invention's ultraviolet-absorbing compounds are directed toward formulations and applications in any art that serve to protect against UV radiation. Exemplary uses of the ultraviolet-absorbing compounds are in adhesive, agriculture, cleaning/polishing, coating, containers, encapsulation, fragrances, imaging, hoses/tubing, household/industrial/institutional, medical, membrane, molded parts, oilfield, packaging, personal care, personal protective equipment, pharmaceutical, printing, veterinary, and wood-care applications. Highly preferred uses of the ultraviolet-absorbing compounds are in personal care and performance chemicals.

2. Description of Related Art

It is now generally accepted that ultraviolet (UV) radiation can be a serious health hazard. Even a limited exposure to solar radiation can cause short- and long-term skin damage, such as erythema, burns, wrinkles, lentigo ("liver spots"), skin cancers, keratotic lesions, and other cellular changes. There is a greater risk for developing such conditions for those who send prolonged time in the sun, such as for their occupation or during recreation.

UV radiation is just one portion of the electromagnetic spectrum, with wavelengths from about 100 nm and about 400 nm, and is further divided into three subregions. UV-A radiation, from about 320 nm to about 400 nm, has the longest wavelength within the UV spectrum, and consequently is the least energetic. While UV-A rays can induce skin tanning, they are liable to induce adverse changes as well, especially in the case of sensitive skin or of skin which is continually exposed to solar radiation. In particular UV-A rays cause a loss of skin elasticity and the appearance of wrinkles, leading to premature skin aging. UV-B rays have shorter wavelengths, from about 290 nm to about 320 nm, and their higher energy can cause erythema and skin burns which may be harmful. The third subgroup, UV-C has the shortest wavelengths, from about 200 nm to about 290 nm, and the highest energy. The Earth's ozone layer effectively filters much UV-C radiation from reaching the ground. Nonetheless, UV-C rays can be generated from tanning bed devices.

In addition to harming the skin, UV radiation can injure the hair, resulting in color changes (especially for color-treated hair), embrittlement, and a loss in aesthetics (e.g., shine, manageability).

UV radiation damage is not limited to the skin and hair, as inanimate objects exposed to solar radiation can experience changes related to color, hardness, and structural integrity, which can contribute to aesthetical and functional deterioration.

Thus, there is the very real and demanding need for compositions that protect the skin, hair, and objects from UV rays, especially UV-A and UV-B radiation. Of special interest are compositions that provide UV-spectrum protection from both UV-A, UV-B, and UV-A and UV-B radiation.

Para-aminobenzoic acid (PABA) exhibits a common trait shared with many UV absorbers/filters. The molecule possesses both electron withdrawing and electron accepting groups, providing resonance delocalization that coincides with the absorbed energy of UV radiation:

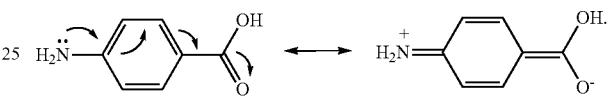

However, PABA is a highly polar molecule, making it water soluble, and giving it a low persistence, meaning that it is not highly retained on the skin after swimming or perspiring. In addition, due to extensive intermolecular bonding, PABA exists as a solid, which may further complicate its formulation. Thus, there exists the need to improve the persistence of UV absorbers, especially those that are water-soluble, and to provide formulation flexibility.

UV absorbers may exhibit photolability, in which the absorbed energy causes photodegradation and/or photoreactivity, and thus reduce its efficacy. Such photolability may result from irreversible isomerisms (i.e., keto-enol tautomerism and cis-trans isomerism), photocleavage, and/or photoaddition, and may be formulation sensitive, (e.g., blends of avobenzone and octinoxate). Examples of photolabile UV absorber include, without limitation: avobenzone, PABA derivatives, cinnamates, and dibenzoyl methane derivatives, all of which degrades over time, and reduce UV protection. Hence, there exists a need to stabilize UV absorbers from photodegradative effects.

Additionally, there exists the need to enhance the efficacy of UV absorbers without increasing their content in the formula, since a maximum addition level frequently is regulated. This efficacy need is especially important for avobenzone, a highly effective UV-A absorber. Avobenzone is subject to keto-enol isomerization due to formulation dependencies (e.g., solvent, other UV absorbers):

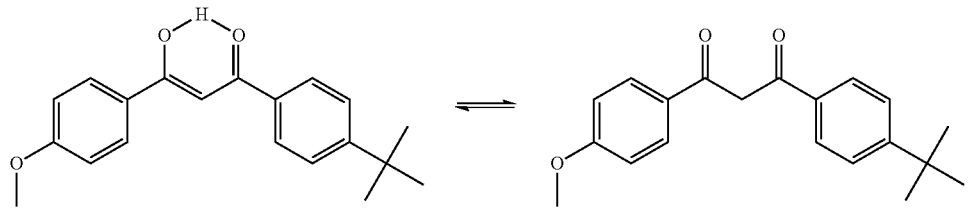

The enol tautomer (left) has its maximum absorbance at 357 nm, which identifies it as a UV-A absorber. Unfortunately, avobenzone is subject to bimolecular reactions (e.g., via cleavage mechanisms) that alter the molecule's structure and decrease its effectiveness as an UV absorber. Hence, an effective method is needed for stabilizing labile UV absorbers like avobenzone in order to enhance their efficacy without increasing their addition level.

Finally, there exists an important need to reduce the migration and skin penetration effects of UV absorbers. For example, octocrylene is a clear, viscous liquid that provides effective protection from UV-A and UV-B radiation. Yet, octocrylene can penetrate the epidermis, where it can act as a photosensitizer and indirectly lead to free-radical damage (Hanson et al., 2006). The desirable protecting properties of UV absorbers like octocrylene would be enhanced if their skin penetration were reduced and/or eliminated.

Amine-containing compositions that stabilize UV absorbers are known in the prior art. For example, stabilized polyolefin-based polymers are taught in U.S. Pat. No. 4,104,248 having the general formula:

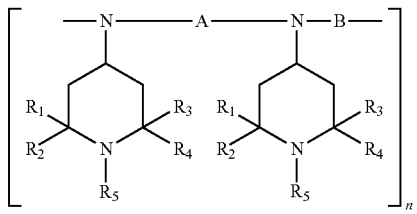

wherein $R_1$, $R_2$, $R_3$, and $R_4$ are equal to or different from each other and are C1-C4 alkyl groups, $R_5$ is hydrogen or a C1-C4 alkyl group, A is a C2-C10 alkylene group, B is a divalent aliphatic, cycloaliphatic, aromatic, or alkylaromatic radical that may contain hetero atoms such as O, S, N, and P, and n is a whole number between 2 and 1000. Compositions of that invention find application in yarns, raffia, ribbons, and shaped articles.

Polyalkylenenaphthalene-2,6-dicarboxylates having reduced fluorescence are provided in U.S. Pat. No. 6,001,952.

U.S. Pat. No. 6,492,455 discloses aqueous solutions comprising the reaction product of a $C_6$+ alpha-olefin/maleic anhydride copolymer with a polyfunctionalized secondary or tertiary amine. The disclosure includes a water-proof sunscreen composition wherein a reaction product of the '455 invention is mixed with benzophenone-3 and octocrylene; the former UV absorber is not covalently bonded to the polymeric reaction product.

Functionalized poly(alpha-olefin-maleic anhydride) polymers are the subject of application PCT/EP2007/051697. This functionalized copolymer has the structure:

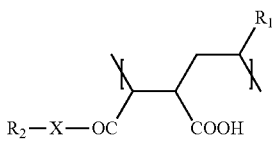

wherein —X— is —O— or —NH—, and —X—$R_2$— is a functional radical selected from a group that includes natural molecules that are UV absorbers, such as tannins, flavonoids, thymol, caffeic acid esters, and vitamin E.

UV-containing polymers are disclosed in the prior art, primarily for industrial applications. Stabilizers for synthetic resins produced from monochlorocyanurates are provided in U.S. Pat. No. 4,698,381. Polymers to eliminate laundry dye transfer are described in U.S. Pat. No. 6,008,316. Ink compositions are provided in U.S. Pat. Nos. 6,059,870; 7,084,189; and U.S. Pat. No. 7,435,291.

U.S. Pat. No. 4,882,412 describes molded plastic compositions produced from the copolymerization of a benzopyran. The compounds are essentially colorless and are directed to untinted packaging materials. Water-dispersible polymeric compounds containing an optical brightener are provided in U.S. Pat. No. 6,150,494 for use in inks, paints, and film forming compositions, especially those compositions for security marking or tagging. The optical brightener comprises at least one polyester reactive group.

Water-borne acrylic polymers are taught in U.S. Pat. No. 6,150,494 and WO 2000/078864 for surface coatings and colorants produced from a vinyl ester monomer and a polymeric fluorescent compound comprising repeating units of residues of: (a) a monomer comprising a dicarboxylic acid or ester, (b) a monomer comprising a diol, diamine or a mixture thereof, (c) a monomer comprising at least one sulfonate group and at least one polyester reactive group, and (d) a monomer comprising an optical brightener agent having at least one polyester reactive group. Personal care applications are not disclosed.

Despite advances in UV absorber technology and formulation development, there remains an unmet need for novel UV absorber compositions, especially those that can provide broad UV-spectrum protection, provide improved waterproofness, stabilize UV absorbers from photodegradative effects, and/or reduce skin penetration tendency. Surprisingly, the ultraviolet-absorbing compounds disclosed address these needs.

SUMMARY OF THE INVENTION

A new class of materials is disclosed that absorbs ultraviolet (UV) radiation. By a first embodiment, the ultraviolet-absorbing compound is derived from at least one first reactant being a UV absorber comprising a carbon-nitrogen triple bond and at least one second reactant comprising amine functionality. By a second embodiment the ultraviolet-absorbing compound is derived from at least one first reactant being a UV absorber comprising amine functionality and at least one second reactant comprising a carbon-nitrogen triple bond. In both embodiments of the invention the reactant that is not the UV absorber may be a small molecule, a monomer, a macromolecule, a biomolecule, or a polymer.

Through judicious selection of reactants, a broad range of functional properties can be designed into the ultraviolet-absorbing compounds. For example, these properties include (without limitation): specification of the UV-spectrum protection, solubility, water-resistance, emolliency, hydration, shine, skin penetration, color, fragrance, glass transition temperature, hardness, and texture. Such ultraviolet-absorbing compounds are directed toward formulations and applications that serve to protect against UV radiation. Exemplary uses of the ultraviolet-absorbing compounds are in adhesive, agriculture, cleaning/polishing, coating, containers, encapsulation, fragrances, imaging, hoses/tubing, household/industrial/institutional, medical, membrane, molded parts, oilfield, packaging, personal care, personal protective equipment, pharmaceutical, printing, veterinary, and wood-care applications.

Remarkably, single ultraviolet-absorbing compounds can be produced that provide both UV-A and UV-B protection, providing enhanced UV protection while simultaneously reducing formulary burden. Even more surprisingly, UV absorbers that exhibit migration effects, such as skin penetration by octocrylene, may be prepared as ultraviolet-absorbing compounds of lower migration, thus increasing their effectiveness. Additionally, UV absorbers that demonstrate light instability, such as avobenzone, may be stabilized when formulated with ultraviolet-absorbing compounds of this invention.

In highly preferred embodiments the ultraviolet-absorbing compounds comprise polymers that find application in the personal care and performance chemicals arts.

DETAILED DESCRIPTION OF PREFERRED EMBODIMENTS OF THE INVENTION

As used herein, the following terms have the meanings set out below:

The terms ultraviolet and UV mean electromagnetic radiation, especially solar electromagnetic radiation, with a wavelength from about 100 nm to about 400 nm, and includes the UV-A, UV-B, and UV-C subclassifications of such radiation.

The term UV-A means ultraviolet electromagnetic radiation with a wavelength from about 320 nm to about 400 nm, and includes UV-A1 (from about 340 nm to about 400 nm) and UV-A2 (from about 320 nm to about 340 nm).

The term UV-B means ultraviolet electromagnetic radiation with a wavelength from about 290 nm to about 320 nm.

The term UV-C means ultraviolet electromagnetic radiation with a wavelength from about 200 nm to about 290 nm.

The term UV absorber means any entity that absorbs, scatters, and/or reflects UV radiation.

The term direct bond means that the group can be nothing.

The term halogen refers to chloro, bromo, iodo and fluoro, and is preferably bromo or chloro.

The term carbon-nitrogen triple bond refers to the group represented by the structure C≡N, and include molecules that may be named as cyano and nitrile.

The term heteroatom refers to atoms such as oxygen, nitrogen, sulfur, and phosphorus.

The term inert solvent refers to a solvent that does not interfere chemically with the reaction.

The term small molecule refers to two or more atoms held together by covalent bonds, typically with a molecular weight less than about 2000 g/mol.

The term monomer refers to a repeating unit chemically bonded to other molecules, such as other monomers. Typically, a monomer is a small molecule.

The term polymer refers to a molecule that contains two or more identifiable structural repeating units of the same or different formula connected by covalent chemical bonds. By this definition polymer comprises those molecules with repeating units ranging from very few to very many.

The term macromolecule refers to any large molecule, which includes polymers.

The term biomolecule refers to any molecule produced by a living organism (or its synthetic analogue), and includes subcategories such as small molecules (e.g., carbohydrates, lipids, hormones), monomers (e.g., amino acids, monosaccharides), oligomers (e.g., fats and oils), polymers (e.g., polysaccharides, lignin, proteins), and macromolecules (e.g., polypeptides).

The term homopolymer refers to a polymer comprising a single monomer.

The term non-homopolymer refers to a polymer comprising two or more monomers and includes essentially all polymers that are not homopolymers. Nonlimiting examples of non-homopolymers include copolymers, terpolymers, tetramers, and the like, wherein the non-homopolymer may be a random, blocked, or alternating polymer.

The term free radical addition polymerization initiator refers to a compound used in a catalytic amount to initiate a free radical addition polymerization. The choice of initiator depends mainly upon its solubility and its decomposition temperature.

The term personal care composition refers to illustrative nonlimiting compositions such as skin, sun, oil, hair, cosmetic, and preservative compositions, including those to protect or alter the appearance, color and feel of skin, hair, and nails. Potential personal care compositions include, but are not limited to, molecules (especially polymers) for increased flexibility in styling, durable styling, increased humidity resistance for hair, skin, and color cosmetics, sun care waterproof/resistance, wear-resistance, and thermal protecting/enhancing compositions. Personal care compositions also may be used to color or lighten skin and hair.

The term effective amount refers to an amount of a composition sufficient to induce a desired result. The result may be the alleviation of the signs, symptoms, or causes of a condition or disease state, and includes, but is not limited to the skin and hair of a subject under treatment. It is understood that the precise amount will vary depending on a variety of factors, such as the age and size of the subject, the condition or disease state being treated, and the treatment being effected.

The term sun-care composition refers to personal care and/or pharmaceutical compositions comprising an effective amount of UV-absorbing compositions, including the ultraviolet-absorbing compounds of this invention. Sun-care compositions include beach and non-beach products that are applied to the face, décolleté, lips, hands, and to skin in general to treat and/or protect against erythema, burns, wrinkles, lentigo ("liver spots"), skin cancers, keratotic lesions, and cellular changes of the skin; and to hair to treat and/or protect against color changes, lack of luster, tangles, split ends, unmanageability, and embrittlement.

The term performance chemicals composition refers to compositions that serve a broad scope of non-personal care applications, and include nonlimiting compositions such as: adhesives, agricultural, coatings, electronics, household-industrial-institutional (HI&I), inks, membranes, metal fluids, oilfield, paper, paints, plastics, printing, plasters, and wood-care compositions.

All percentages, ratio, and proportions used herein are based on a weight basis unless other specified.

Embodiment 1

In the first embodiment of the invention, the ultraviolet-absorbing compound is synthesized by reacting at least one first reactant being a UV absorber comprising a carbon-nitrogen triple bond with at least one second reactant comprising amine functionality. Such reactions are known to one skilled in the art, and an interested reader is referred to one of the many texts on the subject, such as Organic Chemistry by Morrison and Boyd (1992), which is hereby incorporated in its entirety by reference.

First Reactant, UV Absorber Comprising Carbon-Nitrogen Triple Bond

An especially preferred family of first reactants (i.e., UV absorbers) that meets the requirements of the first embodiment of the invention is the family of cyanoacrylates, including the structure represented below:

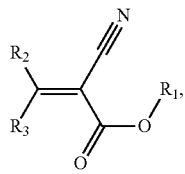
(1)

wherein $R_1$, and $R_3$ are independently selected from hydrogen, functionalized and unfunctionalized alkyl, cycloalkyl, alkenyl, and aryl groups, wherein any of the before mentioned groups may be present with or without heteroatoms; and wherein $R_2$ is independently selected from hydrogen, halogen, functionalized and unfunctionalized alkyl, cycloalkyl, alkenyl, and aryl groups, wherein any of the before mentioned groups may be present with or without heteroatoms. The alkyl and alkenyl groups may be branched or unbranched (straight-chain). Preferably, the alkyl and alkenyl groups are $C_1$-$C_{60}$, more preferably $C_1$-$C_{36}$, and most preferably $C_1$-$C_{18}$ groups. Cycloalkyls (closed rings) include cyclopentane, cyclohexane, cycloheptane, and the like. Aryl groups include benzenes, naphthalenes (two rings), and anthracenes (three rings), and the like.

In structure (1) it is preferred that at least one of $R_2$ or $R_3$ comprises an aryl group:

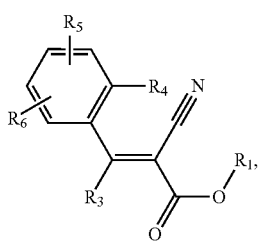
(2)

or $R_2$ and $R_3$ both comprise aryl groups:

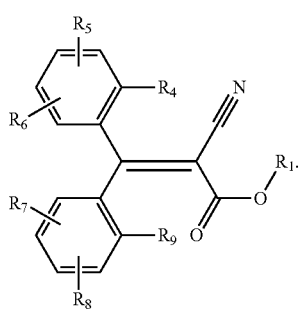
(3)

In structures (2) and (3) one or more of the aryl groups may be substituted, wherein $R_1$ and $R_3$ are independently selected from hydrogen, functionalized and unfunctionalized alkyl, cycloalkyl, alkenyl, and aryl groups, wherein any of the before mentioned groups may be present with or without heteroatoms; and wherein $R_4$, $R_5$, $R_6$, $R_7$, $R_8$, and $R_9$ are independently selected from hydrogen, halogen, functionalized and unfunctionalized alkyl, cycloalkyl, alkenyl, and aryl groups, wherein any of the before mentioned groups may be present with or without heteroatoms.

Two specific examples of structure (3) find special application in the invention. The first example, etocrylene, is obtained when $R_1$ is an ethyl group, and $R_4$, $R_5$, $R_6$, $R_7$, $R_8$, and $R_9$ are hydrogen:

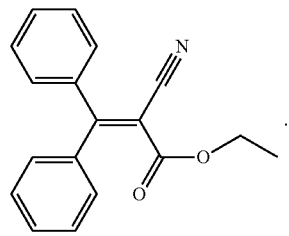 [SMILES: CCOC(=O)C(C#N)=C(c1ccccc1)c1ccccc1]

Etocrylene, also known as ethyl-2-cyano-3,3-diphenylacrylate, is a UV absorber that finds application in performance chemicals applications.

A second example of structure (3) is octocrylene, provided when $R_1$ is an ethylhexyl group, and $R_4$, $R_5$, $R_6$, $R_7$, $R_8$, and $R_9$ are hydrogen:

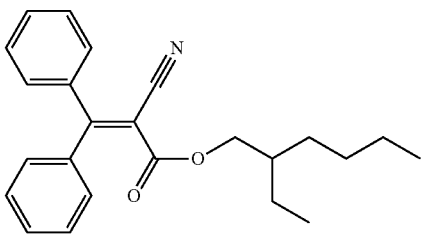

Octocrylene is also known as 2-ethylhexyl-2-cyano-3,3-diphenylacrylate, and is widely used in personal care applications. It has been approved for human use in many countries, including Australia/New Zealand, Canada, the EU, Japan, and the US.

Within the first embodiment, the first reactant is not limited to UV absorbers wherein the carbon-nitrogen triple bond is native to the molecule. Contemplated is the chemical modification of other UV absorbers as to incorporate a carbon-nitrogen triple bond into the molecule and thus provide the necessary reactivity described for this embodiment of the invention.

Second Reactant Having Amine Functionality

In addition to at least one UV absorber containing a carbon-nitrogen triple bond, the ultraviolet-absorbing compounds of the first embodiment also are derived from at least one second reactant having amine functionality. Amines are molecule that possess at least one nitrogen atom, and are classified by the number of hydrogen atoms attached thereto. For example, primary amines have two hydrogen atoms and one non-hydrogen group bonded to the nitrogen atom, secondary amines have one hydrogen atom and two non-hydrogen groups bonded to the nitrogen atom, and tertiary amines have three non-hydrogen atoms bonded to the nitrogen atom. Any number and combination of these amine groups can be used.

Preferred, and without limitation, are primary and secondary amines.

Additionally, the amine molecule can be aliphatic or heterocyclic. Aliphatic amines are those compounds without a ring structure, and include alkane, alkene, and alkyne bonding constructs. Both linear and branched aliphatic amines are known. Heterocyclic amines are those compounds wherein at least one nitrogen atom comprises part of a ring structure. The term heterocyclic means that the nitrogen atom resides in the ring with non-nitrogen atoms, including, but not limited to: carbon, hydrogen, other nitrogen, oxygen, and sulfur atoms. Examples of suitable heterocyclic amines include imidazole and its derivatives.

Both aliphatic and heterocyclic amines are known to exist in linear, branched, and even hyperbranched molecular arrangements. To avoid any arbitrary delineation between the types, as used henceforth, the term branched is taken to mean all non-linear molecular arrangements, such as branched and hyperbranched.

This second reactant can be a small molecule, a monomer, a polymer, a macromolecule, or a biomolecule.

In preferred examples of this first embodiment, this second reactant comprises a small molecule or a monomer. Many such molecules are known in the various arts where protection from UV radiation is sought, including the personal care and performance chemicals arts. Examples of amine-containing small molecules include those compounds in the following list, which is not intended to be all-inclusive: 4-methyl-6-(phenylazo)-1,3-benzenediamine; 1,3-dimethylpentylamine; 1-naphthylamines and 2-naphthylamines; 2,2,6-trimethyl-4-piperidyl benzoate (benzamine); 2,4-diaminodiphenylamine; 2,6-bis(2-hydroxyethoxy)-3,5-pyridinediamine; 2,6-dimethoxy-3,5-pyridinediamine HCl; 2,6-dimethyl-p-phenylenediamine; 2,6-dimethyl-p-phenylenediamine HCl; 2-chloro-5-nitro-N-hydroxyethyl-p-phenylenediamine; 2-chloro-p-phenylenediamine; 2-methyl-m-phenylenediamine; 2-methylheptylamine(2-(N-methyl)heptylamine); 2-nitro-p-phenylenediamine; 2-phenylbenzimidazole-5-sulphonic acid; 3,4,5-trimethoxyphenetylamine; 4,4'-diaminodiphenylamine; 4,4'-[(4-methyl-1,3-phenylene)bis(azo)]bis[6-methyl-1,3-benzenediamine]; 4-ethoxy-m-phenylenediamine; 4-methyl-m-phenylenediamine; 4-nitro-in-phenylenediamine; 4-nitro-o-phenylenediamine; 4-nitro-o-phenylenediamine dihydrochloride; 4-nitro-o-phenylenediamine HCl; 4-nitro-o-phenylenediamine sulfate; 6-(piperidinyl)-2,4-pyrimidinediamine-3-oxide (minoxidil); 6-methoxy-2,3-pyridinediamine; 6-nitro-2,5-pyridinediamine; acetyl glucosamine; acetyl glutamine; alanyl glutamine; behenamidopropyl dimethylamine; benzoguanamine; biotin/folic acid/cyanocobalamin/niacinamide/pantothenic acid/pyridoxine/riboflavin/thiamine/yeast polypeptides; biphenyl-2-ylamine; biphenyl-4-ylamine; cetylamine hydrofluoride; chloramine T; cyclohexylamine; cysteamine HCl; dibehenyl methylamine; dihydroxyethyl tallowamine oxide; dimethylamine; diphenylamine; dipropylenetriamine; ethanolamine thioglycolate; ethyl ethanolamine; gases (petroleum) from amine system feed; glucamine; glucosamine; glucosamine ascorbate; glucosamine HCl; glucosamine salicylate; glucosamine thioctate; glutamine; hydrogenated tallowamine (CAS #61788-45-2); hydroxyethyl-p-phenylenediamine sulfate; hydroxylamine HCl; hydroxylamine sulfate; isopropanolamine; isopropylamine; isopropylamine dodecylbenzenesulfonate; isostearamidopropyl dimethylamine; isostearamidopropyl dimethylamine lactate; lauramine(1-aminododecane); lauraminopropylamine; laurylamine dipropylenediamine; m-phenylenediamine; m-phenylenediamine, mecamylamine; melamine/formaldehyde resin; methoxypolyoxymethylene melamine; methylethanolamine; methylglucamine; monoalkylamines, monoalkanolamines; myristamidopropyl dimethylamine; myristamidopropylamine oxide; N,N'-bis(2-hydroxyethyl)-2-nitro-p-phenylenediamine; N,N'-dimethyl-N-hydroxyethyl-3-nitro-p-phenylenediamine; N,N-bis(2-hydroxyethyl)-p-phenylenediamine sulfate; N,N-diethyl-p-phenylenediamine; N,N-dimethyl-p-phenylenediamine; N-(2-methoxyethyl)-p-phenylenediamine; N-methyl-3-nitro-p-phenylenediamine; N-phenyl-p-phenylenediamine; N-phenyl-p-phenylenediamine HCl; N-phenyl-p-phenylenediamine sulfate; N-(2-hydroxyethyl)-4-nitro-o-phenylenediamine; N-(tris(hydroxymethyl)methyl-4-nitro-1,2-phenylenediamine; o-phenylenediamine; octamylamine; oleamidopropyl dimethylamine; oleamine; p-phenylenediamine; p-phenylenediamine HCl; p-phenylenediamine sulfate; N-substituted derivatives of o-phenylenediamine; palmitamine; polyoxymethylene melamine; polyoxymethylene melamine urea; secondary alkyl- and alkanolamines; sodium bischlorophenyl sulfamine; stearamidoethyl ethanolamine; stearamidoethyl ethanolamine phosphate; stearylamine; thiamine diphosphate; thiamine HCl; thiamine nitrate; toluene-2,5-diamine; toluene-2,5-diamine sulfate; toluene-3,4-diamine; trisodium ethylenediamine disuccinate; tromethamine, isododecyl ether diamine (Adogen® 582, Adogen® 583); hydrogenated tallow diamine (Adogen® 540); coca diamine (Adogen® 560); tallow diamine (Adogen® 570S); tallow triamine (Adogen® 670, Adogen® 770); hydrogenated tallow amine (Adogen® 140, 140D); palmityl amine (Adogen® 141, 141D); stearyl amine (Adogen® 142); coco amine (Adogen®160, 160D); ethoxylated coco amine (Adogen® 160 D EO); lauryl amine (Adogen® 163, 163D); tallow amine (Adogen® 170); ethoxylated tallow amine (Adogen® 170 D EO); oleyl amine (Adogen® 172); isododecyl ether amine (Adogen® 182); isotridecyl ether amine (Adogen® 183); di-iso tridecyl amine (Adogen® 283); di-hydrogenated tallow methyl amine (Adogen® 343 HP); di-stearyl methyl amine (Adogen® 249); tri(C8-C10) amine (Adogen® 364); di-coco methyl amine (Adogen® 369); PEG-2 cocamine (Varonic® K202); PPG 2 cocamine (Varonic® K202 P); PEG-5 cocamine (Varonic® K205); PEG-10 cocamine (Varonic® K210); PEG-15 cocamine (Varonic® K215); PEG-2 oleyl amine (Varonic® Q202); PEG-2 stearyl amine (Varonic® S202); PEG-2 tallow amine (Varonic® T202); PPG-2 tallow amine (Varonic® T202 P); PEG-3.5 tallow amine (Varonic T2035); PEG-5 tallow amine (Varonic® T205); PEG-10 tallow amine (Varonic® T210); PEG-15 tallow amine (Varonic® T215); PEG-20 tallow amine (Varonic® T220); PPG-2 tallow diamine (Varonic® T402 P); PEG-3 tallow diamine (Varonic® T403); or PEG-2 hydrogenated tallow amine (Varonic® U202).

In another preferred example of this first embodiment, the second reactant having amine functionality comprises a polymer. These groups can occur anywhere in the polymer, including, but not limited to, one or more: end groups, side chains, grafted units, pendant groups, repeating units of any configuration (e.g., alternating, block, random), or on the polymer backbone.

One highly preferred aminopolymer is the family of polyether amines, such as the Jeffamine® product line offered for commercial sale by Huntsman Corporation (Everberg, BE). A review of this product line is presented in a published sales brochure titled, "The Jeffamine® Polyetheramines," which is incorporated herein in its entirety by reference. These polymers are primarily based on ethylene oxide (EO) and/or propylene oxide (PO), and contain one, two, or three primary amine groups per molecule.

A desirable feature of the Jeffamine® polyether amines is the range of properties attainable by customizing the polymerizable units, ratio of EO/PO, and molecular weight. For example, the Jeffamine® ED series possesses a polyethylene glycol-based backbone, and is completely water soluble, while various "experimental amines" are oleophilic and not water soluble. Hence, these polyether amines are contemplated singly and in blends in order to attain targeted properties in the ultraviolet-absorbing compound product.

The Jeffamine® family of polymers also offers chemical flexibility by offering different numbers of amine groups per molecule, including (but are not limited to) polyether monoamines (e.g., Jeffamine® M series), polyether diamines (e.g., Jeffamine® D, ED, and EDR series) and polyether triamines (e.g., Jeffamine® T series). These different polymer families allow formulation and product flexibility while maintaining essentially the same base chemistry. For example, a higher amount of UV absorber can be covalently bonded into the molecule using polyether triamines than polyether monoamines. Hence, product can be made for the full range of sun protection factors, e.g., UV boosters to UV blockers, based on one type of chemistry, which may simplify formulation and product development.

This discussion of polymer backbone chemistry and number of amine groups per molecule is not unique to the Jeffamine® family, as one skilled in the art will recognize that these details can extend to other polymer families as well.

For example, polyethyleneimine is well known to those skilled in the art, and a description is provided in *Kirk-Othmer Encyclopedia of Chemical Technology*, third edition, volume 20, 1982, pages 214-216, which is incorporated herein by reference. The use of polyethyleneimines with primary and secondary amine functionality is contemplated. Linear, branched, and hyperbranched polyethyleneimines are commercially available from Polysciences, Inc. (Warrington, Pa.). Typical polyethyleneimine molecular weights range from about 1,200 g/mol to 100,000 g/mol, although polyethyleneimines with molecular weights outside this range are known to those skilled in the art.

Aminofunctional silicones represent another class of polymers that find application in this invention. Broadly speaking, these polymers contain at least one amine group and at least one silicon atom. These polymers represent a broad array of chemistries that may be ideal for creating the disclosed ultraviolet-absorbing compounds. For example, aminoalkylsiloxanes and aminoalkoxysiloxanes are but two examples of this polymer family, which can be further reacted to yield chemistries that include polyimides, polyureas, and polyurethanes.

Examples of aminofunctional silicones include isostearamidopropyl dimethylamine gluconate (and) propylene glycol amine-functional silicones; offered for commercial sale by The Lubrizol Corporation (Wickliffe, Ohio). Also available are a number of aminopropyl-terminated polydimethylsiloxanes, N-ethylamino-isobutylterminated-polydimethylsiloxanes, aminopropylmethylsiloxane-dimethylsiloxane copolymers, aminoethyl-aminopropylmethylsiloxane-dimethylsiloxane copolymers, aminoethyl-aminoisobutyl-methylsiloxane-dimethylsiloxane copolymers, and aminoethyl-aminopropylmethoxysiloxane-dimethylsiloxane copolymers, all of which are offered for commercial sale by Gelest, Inc. (Morrisville, Pa.). Blends of polymers having amine units also are contemplated.

As indicated in the above lists, homopolymers and non-homopolymers, including copolymers and terpolymers, of the aminopolymers are contemplated for use in this invention. Also suitable are polymer blends provided at least one polymer comprises amine functionality.

Further examples of suitable amino polymers include, but are not limited to the amino polymers disclosed in U.S. Pat. Nos. 5,270,379; 5,373,052; 5,496,545; 5,624,963; 5,667,775; 5,679,717; 5,693,675; 5,703,188; 6,008,316; US patent application 2009/0012241; PCT application WO 2008/066849, all of which are incorporated herein their entirety by reference.

While the ultraviolet-absorbing compounds preferably are synthesized when the second reactant is small molecule, a macromolecule or a polymer, the ultraviolet-absorbing compounds also can be prepared from a second reactant having one or more polymerizable units with amine functionality. This aspect of the invention encompasses amine units that are polymerizable by known methods, including without restriction: condensation polymerization, free radical polymerization, emulsion polymerization, ionic chain polymerization, and precipitation polymerization.

Examples of polymerizable units having amine functionality include, but are not limited to:
  N-aminoalkyl(meth)acrylamides and derivatives (e.g., N-aminoethyl(meth)acrylamides, N-aminopropyl(meth)acrylamides),
  N-alkylamino-N-alkyl(meth)acrylamides and derivatives (e.g., N-methyl-N-aminomethyl(meth)acrylamide, N-methyl-N-aminopropyl(meth)acrylamide),
  alkylamino(meth)acrylates and derivatives (e.g., 2-aminoethyl(meth)acrylate, 3-aminopropyl(meth)acrylate),
  and blends thereof these polymerizable units.

Within the first embodiment, the second reactant is not limited to compounds wherein the amine group is native to the molecule. Contemplated is the chemical modification of otherwise non-reactive second reactants as to incorporate amine functionality into the molecule and thus enable the necessary reactivity described for this embodiment of the invention.

Because the second reactant can exhibit such a broad diversity of chemistries, it will be appreciated that the synthesized ultraviolet-absorbing compounds can find application in a broad assortment of fields, including: adhesive, agriculture, cleaning/polishing, coating, containers, encapsulation, fragrances, imaging, hoses/tubing, household/industrial/institutional, medical, membrane, molded parts, oilfield, packaging, personal care, personal protective equipment, pharmaceutical, printing, veterinary, and wood-care applications. Thus, the synthesis, formulation, production and use of ultraviolet-absorbing compounds to serve into these applications are contemplated.

Embodiment 2

Novel ultraviolet-absorbing compounds of the invention also are described by a second embodiment. They may be synthesized by reacting at least one first reactant being a UV absorber having amine functionality with at least one second reactant possessing a carbon-nitrogen triple bond.

First Reactant, UV Absorbers Having Amine Functionality

UV absorbers comprising at least one amine group are known, and include the following compounds: benzophenone-5; bisdisulizole disodium (Neo Heliopan® AP); diethylhexyl butamido triazone (iscotrizinol); menthyl anthranilate (meradimate); p-aminobenzoic acid; phenylbenzimidazole sulfonic acid (ensulizole, Eusolex® 232); N,N'-bisformyl-N,N'-bis-(2,2,6,6-tetramethyl-4-piperidinyl)-hexamethylendiamine (Uvinul® 4050 H); bis-(2,2,6,6-tetramethyl-4-piperidyl)-sebacate (Uvinul® 4077 H, Uvinul® 4077 GR); sterically-hindered amine CAS #152261-33-1; 2,6-di-tert-butyl-4-[4,6-bis(octylthio)-1,3,5-triazin-2-ylamino]phenol (Irganox® 565); N,N'-hexane-1,6-diylbis[3-(3,5-di-tert-butyl-4-hydroxyphenylpropionamide)] (Irganox® 1098); and N-phenyl-benzenamine reaction products with 2,4,4-trimethylpentene (Irganox® 5057).

Within the second embodiment, the first reactant is not limited to UV absorbers wherein the amine group is native to the molecule. Contemplated is the chemical modification of otherwise non-reactive UV absorbers as to incorporate amine functionality into the molecule and thus enable the necessary reactivity described for this embodiment of the invention.

Second Reactant have Carbon-Nitrogen Triple Bond

In addition to at least one UV absorber containing amine functionality, the ultraviolet-absorbing compounds of the second embodiment of this invention also are derived from at least one molecule comprising a carbon-nitrogen triple bond.

This second reactant can be a small molecule, a monomer, a polymer, a macromolecule, or a biomolecule.

In a preferred embodiment of this second embodiment, this second reactant having a carbon-nitrogen triple bond is a small molecule. Many such small molecules are known in the arts where UV radiation protection is sought, including the personal care and performance chemicals arts.

Examples of small molecules having a carbon-nitrogen triple bond include those compounds in this list, which is not intended to be all-inclusive: acetonitrile; acrylonitrile; adiponitrile alkali pentacyanonitrosylferrate; p-anisonitrile; benzonitrile; biotin/folic acid/cyanocobalamin/niacinamide/pantothenic acid/pyridoxine/riboflavin/thiamine/yeast polypeptides; butadiene/acrylonitrile copolymer; p-tert-butylphenyl acetonitrile; α-chloroacrylonitrile; cinnamonitrile (cis and trans); citronellyl nitrile; cuminyl nitrile; crotonitrile; cyanocobalamin; 4-cyano-2,6-diiodophenyl octanoate; cyanotis arachnoidea root extract; decanenitrile; dibromocyanoacetamide; 2,6-dibromo-4-cyanophenyl octanoate; 3,5-dibromo-4-hydroxybenzonitrile; 1,3-dimethyl-bicycloheptane-2-carbonitrile; 2,4-dimethyl cyclohexenecarbonitrile; 3,5-dimethyl cyclohexenecarbonitrile; 2,3-dimethyl-2-nonenenitrile; 3,7-dimethyl-octanenitrile; dodecanenitrile; ethacrylonitrile; ethyl cyanoacrylate; 4-ethyl-α,α-dimethylbenzenepropanenitrile; fumarodinitrile; fumaronitrile; 6-hydroxy-1-(3-isopropoxypropyl)-4-methyl-2-oxo-5-[4-(phenylazo)phenylazo]-1,2-dihydro-3-pyridinecarbonitritle; glutaronitrile; hexenyloxy-propanenitrile; homogeranyl nitrile; isobutyronitrile; isopropyl cyanoacrylate; 7-isopropyl-5-methylbicyclooctene-2-carbonitrile; maleodinitrile; malononitrile; methacrylonitrile; methallyl cyanide; 3-methyl-2-butenonitrile; γ-methyl benzenehexanenitrile; methyl cinnamonitrile; methyl cyanoacetate α-methyldecanenitrile; 3-methyldodecanonitrile; 2-methylene glutaronitrile; 3-methylnon-2-enenitrile; 3-methyl-5-phenyl-2-pentenenitrile (cis and trans); trans-3-methyl-5-phenyl-2-pentenenitrile; α-methyl-α-vinyl-benzenepropanenitrile; myclobutanil; 2-(4-chlorophenyl)-2-(1H-1,2,4-triazol-1-ylmethyl)hexanenitrile; nitriles coco; non-2-enenitrile; octahydro-8,8-dimethylnaphthalene-2-carbonitrile; phenylacetonitrile; polyoxymethylene cyanoguanidine urea; propacrylonitrile; propioacrylonitrile; succinonitrile; tetramethyl-4,8-decadienenitrile; tridec-2-enenitrile; trimethyl-1-cyclohexenylacrylonitrile; trimethyl-3-cyclopentenylacetonitrile; trimethylbicyclo-3-heptylacrylonitrile; trimethylbicyclohept-3-ylidenepropiononitrile; 2-undecenenitrile; undecenal/cyanoacetatic acid; and vinylidene cyanide.

Blends and combinations of the above small molecules with other molecules (both with and without molecules having a carbon-triple bond) are contemplated.

In an equally preferred embodiment of this second embodiment, this second reactant comprises a polymer. Many such polymers having a carbon-nitrogen triple bond are known in the relevant application arts. Examples of these polymers include those compounds in this list, without limitation:

the family of olefinically unsaturated polynitriles and derivatives, a family that includes (but it not limited to): polyacrylonitrile, polychloroacrylonitrile, polymethacrylonitrile and the like, as well as polypropacrylonitrile, polyglutaronitrile, poly(methylene-glutaronitrile), poly(fumaronitrile)], non-homopolymers [e.g., poly(acrylonitrile-co-butadiene), poly(acrylonitrile-co-methyl methacrylate), poly(acrylonitrile-ter-methacrylonitrile-ter-methyl methacrylate)terpolymer)], poly(acrylonitrile-co-butadiene), polyacrylonitrile-ter-butadiene-ter-styrene), poly(acrylonitrile-ter-butadiene-ter-vinyl chloride)], polymers that optionally may be carboxylated, hydrogenated, and/or crosslinked.

the family of polyether nitriles and derivatives, including (but it not limited to): polyarylene ether nitrile and polymers based on poly(2-cyanophenylene). A polyether nitrile family of polymers is described in an article by A. Saxena et al., which is incorporated herein its entirety by reference.

the family of vinylidene cyanides and derivatives, including (but it not limited to): homopolymers and non-homopolymers of poly(vinylidene cyanide), including those disclosed in U.S. Pat. No. 5,057,588, which is hereby incorporated in its entirety by reference.

the family of cyanoalkylacrylates and derivatives, including (but it not limited to): polymers derived from allyl-2-cyanoacrylate, butyl-2-cyanoacrylate, decyl-2-cyanoacrylate, ethoxyethyl cyanoacrylate, ethyl-2-cyanoacryalte, hexyl-2-cyanoacrylate, isobutyl-2-cyanoacrylate, methyl-2-cyanoacrylate, and propyl-2-cyanoacrylate.

Additionally, ultraviolet-absorbing compounds that conform to the second embodiment of this invention can be prepared from polymerizable units having a carbon-nitrogen triple bond. This aspect of the invention encompasses monomers having carbon-nitrogen triple bonds that are polymerizable by known methods, including without restriction: condensation polymerization, free radical polymerization, emulsion polymerization, ionic chain polymerization, and precipitation polymerization.

These polymerizable units include, without limitation: acrylonitrile; allyl-2-cyanoacrylate; 2,3-butadiene-1-nitrile; butyl-2-cyanoacrylate; chloroacrylonirile; decyl-2-cyanoacrylate; ethacrylonitrile; ethoxyethyl cyanoacrylate; ethyl-2-cyanoacrylate; fumarodinitrile; fumaronitrile; hexyl-2-cyanoacrylate; isobutyl-2-cyanoacrylate; methacrylonitrile; methallyl cyanide; 3-methyl-2-butenenitrile; methyl-2-cyanoacrylate; 3-methyl-3-butenenitrile; 2-methylene glutaronitrile; propyl-2-cyanoacrylate; vinylacetonitrile; 4-vinylbenzonitrile; and vinylidene cyanide.

Within the second embodiment, the second reactant is not limited to those compounds wherein the carbon-nitrogen triple bond is native to the molecule. Contemplated is the chemical modification of otherwise non-reactive second reactants as to incorporate this carbon-nitrogen triple bond into the second reactant and thus enable the necessary reactivity described for this embodiment of the invention.

Because the second reactant can exhibit such a broad diversity of chemistries, it will be appreciated that the synthesized ultraviolet-absorbing compounds can find application in a broad assortment of fields, including: adhesive, agriculture, cleaning/polishing, coating, containers, encapsulation, fragrances, imaging, hoses/tubing, household/industrial/institutional, medical, membrane, molded parts, oilfield, packaging, personal care, personal protective equipment, pharmaceutical, printing, and veterinary applications. Thus, the synthesis, formulation, production and use of ultraviolet-absorbing compounds to serve into these applications is contemplated.

Synthesis of the Ultraviolet-Absorbing Compound

Generally speaking, there are at least three synthesis approaches for preparing the ultraviolet-absorbing compounds of this invention. The first two methods are preferred to create ultraviolet-absorbing polymers according to the invention.

By a first method, when the second reactant comprises a polymerizable unit, then a polymerization reaction first polymerizes (either completely or partially) the second reactant. Then, that product is reacted with the first reactant (i.e., the UV absorber) to synthesize the ultraviolet-absorbing compound.

By a second approach, a first reaction is conducted to covalently bond the first and second reactants when the second reactant comprises a polymerizable unit. During this reaction the polymerizable moiety of the second reactant is preserved. The product from this first reaction is an ultraviolet-absorbing compound of the invention. Nonetheless, it is preferred that a second reaction polymerizes part or all of the polymerizable moieties to create the ultraviolet-absorbing polymer.

Polymerization methods known to one skilled in the art may be employed when the second reactant comprises a polymerizable unit. These methods include solution polymerization, emulsion polymerization, dispersion polymerization, ionic chain polymerization, and precipitation polymerization. Free radical solution polymerization is a preferred polymerization method, especially when using water-dispersible and/or water-soluble reaction solvent(s), and is described in "Decomposition Rate of Organic Free Radical Polymerization" by K. W. Dixon (section II in *Polymer Handbook, volume* 1, $4^{th}$ *edition,* Wiley-Interscience, 1999), which is incorporated by reference. Other polymerization methods may be preferred based on considerations such as final polymer form and ease of production.

Optionally, when the ultraviolet-absorbing compound comprises a polymer, the reactive step(s) may include a crosslinking agent. Addition of one or more crosslinkers may increase the polymer molecular weight, decrease water solubility, and/or produce a gelled product. Crosslinking agents and the use thereof are known to one skilled in the art.

A third approach may be employed when: (a) the second reactant is not a polymer or does not comprise a polymerizable unit (e.g., the second reactant is a small molecule or a biomolecule), and (b) when the second reactant comprises a pre-formed polymer. In this approach the first reactant and the second reactant are reacted to form the described ultraviolet-absorbing compounds without any polymerization reaction step. However, it is noted that the synthesized ultraviolet-absorbing compound need not be a polymer. For example, the second reactant may be a small molecule (as listed above), or a functionalized oligomer, fatty acid, or oil.

Referring now to the first embodiment of the invention, at least one first reactant being a UV absorber bearing a carbon-nitrogen triple bond and at least one second reactant comprising amine functionality are reacted to yield a ultraviolet-absorbing compound. The reactants may be charged together into a reactor and stirred at a temperature to facilitate the reaction, being limited only by the decomposition temperature of any reactant. The reaction can be performed with and without added solvent.

Similarly, referring to the second embodiment of the invention, at least one first reactant being a UV absorber containing amine functionality and at least one second reactant comprising at least one carbon-nitrogen triple bond are reacted to yield a ultraviolet-absorbing compound. The reactants may be charged together into a reactor and stirred at a temperature to facilitate the reaction, being limited only by the decomposition temperature of any reactant. The reaction can be performed with and without added solvent.

It is within the scope of this invention to employ any mixture of UV actives (e.g., UV-A and UV-B actives). It may be advantageous to add the least reactive absorbers first, and the more reactive ones later in the preparation. As necessary, additional reactive species can be attached to the product.

There is great flexibility in selecting the addition levels of the first and second reactants, which results in a wide range of properties for the ultraviolet-absorbing compounds. For example, ultraviolet-absorbing compounds may function as "boosters," providing a sun protection factor of 2 or less, by limiting the amount of UV absorber into the product (e.g., by covalent bonding or molecular entanglements). Conversely, the ultraviolet-absorbing compound may function more like a "sun block," imparting a sun protection factor of 20, 30, 50, or even higher (e.g., 100), by incorporating larger amount of UV absorber (e.g., by covalent bonding or molecular entanglements) into the product.

More specifically, the addition levels of the first and second reactants may range such that either reactant is present in excess (meaning exceeding the stoichiometric reaction amount). For example, a reactor charge ratio of about 99% first reactant (i.e., UV absorber): 1% second reactant (on an effective weight bases) may produce a product of high UV absorber content. Alternatively, a reactor charge ratio of about 1% first reactant (i.e., UV absorber): 99% second reactant (on an effective weight bases) may produce a product of low UV absorber content. More typically, however, the reactor is charged with from about 35% first reactant (i.e., UV absorber): 65% second reactant to about 65% first reactant (i.e., UV absorber): 35% second reactant (effective weight bases).

It may be beneficial and desirable to remove any amount of unreacted reactant (e.g. UV absorber), and/or side product from the final reaction product using methods that are known in the art.

The reaction may be carried out for times ranging from 30 seconds to 48 hours or even more, and may depend upon factors that include (1) the degree of the amine (primary vs. secondary vs. tertiary), (2) the number of amine groups, (3) steric hindrance surrounding the reactive sites of the first and/or second reactants, (4) the reactivity of the UV absorber (s), (5) the reaction temperature employed, (6) the presence or absence of a solvent, and (7) the use or non-use of an initiator and/or catalyst. With the use of an optional reaction solvent or solvents, it may be preferred to remove the solvent(s) after the reaction, e.g., at reduced pressure and/or elevated temperature, and then to add a different solvent conducive to the final formulation.

Typically, the molecular weight of the ultraviolet-absorbing compound ranges from about 200 g/mol to about 5,000,000 g/mol, and more preferably the molecular weight ranges from about 2,000 g/mol to about 1,000,000 g/mol. As described later, the molecular weight of a polymerized product may be modulated by the addition of an optional crosslinking and/or chain transfer agent to the reaction vessel.

For solution reactions, temperatures may be conveniently controlled by judicious choice of solvents within an appropriate boiling range. Temperatures in this case range from 20° C. to about 225° C., preferably from 75° C. to 200° C., and most preferably from 80° C. to 200° C. Reaction times for solvent reaction range from several minutes to 48 hours or more. Higher reaction temperatures and highly reactive reactants will reduce time for conversion to the desired product(s). Preferably, solvent reaction times will be between 15 minutes and 8 hours and most preferably between 15 minutes and 4 hours. In addition, azeotropic water removal (when possible) from the solvent will facilitate most solvent reactions.

The use of certain reactants and selection of reaction temperature may result in a reacting system of high viscosity, which may reduce the reaction yield. A resolution to this problem is the addition of an inert solvent, such as additional reaction solvent.

It is highly preferred that the reaction covalently bond the UV absorber to the second reactant. The synthesized ultraviolet-absorbing compounds may exhibit reduced volatilization, migration, or other mechanisms even at high temperatures. As a result, the compositions of this invention are particularly useful for reducing or essentially eliminating UV active migration (e.g., skin penetration of the UV active) and for extending product service life.

Initiator

In some synthesis routes, an initiator is not needed to produce the ultraviolet-absorbing compounds. One such example is when the first reactant (i.e., UV absorber) comprises octocrylene and the second reactant is an aminopolymer; the reaction can be accomplished by stirring the reactants at room temperature.

Due to the broad nature of the invention, there are times when an free radical addition polymerization initiator may be beneficial. One such example is when the second reactant comprises primary and/or secondary amine group(s). In this case, an initiator may be used.

Compounds capable of initiating the free-radical addition polymerization include those materials known to function in the prescribed manner, and include the peroxo and azo classes of materials. Exemplary peroxo and azo compounds include, but are not limited to: acetyl peroxide; azo bis-(2-amidinopropane)dihydrochloride; azo bis-isobutyronitrile; 2,2'-azo bis-(2-methylbutyronitrile); benzoyl peroxide; di-tert-amyl peroxide; di-tent-butyl diperphthalate; butyl peroctoate; tert-butyl dicumyl peroxide; tert-butyl hydroperoxide; tert-butyl perbenzoate; tert-butyl permaleate; tert-butyl perisobutylrate; tert-butyl peracetate; tert-butyl perpivalate; para-chlorobenzoyl peroxide; cumene hydroperoxide; diacetyl peroxide; dibenzoyl peroxide; dicumyl peroxide; didecanoyl peroxide; dilauroyl peroxide; diisopropyl peroxodicarbamate; dioctanoyl peroxide; lauroyl peroxide; octanoyl peroxide; succinyl peroxide; and bis-(ortho-toluoyl)peroxide.

Also suitable to initiate the free-radical polymerization are initiator mixtures or redox initiator systems, including: ascorbic acid/iron(II) sulfate/sodium peroxodisulfate, tert-butyl hydroperoxide/sodium disulfite, and tert-butyl hydroperoxide/sodium hydroxymethanesulfinate.

Chain Transfer Agent

When a polymerization method is used during the synthesis of the ultraviolet-absorbing compounds, a chain transfer agent optionally may be used to control the degree of polymerization of the polymer, and thereby control the molecular weight and molecular weight distribution of the product according to the present disclosure. As a skilled artisan can appreciate, typically, the chain transfer agent becomes part of the latex polymer.

In exemplary embodiments, the chain transfer agent has a carbon-sulfur covalent bond. The carbon-sulfur covalent bond has usually absorption peak in a wave number region ranging from 500 to 800 cm$^{-1}$ in an infrared absorption spectrum. When the chain transfer agent is incorporated into the polymer, the absorption peak of the product may be changed in comparison to product made without a chain transfer agent.

Exemplary chain transfer agents include, but are not limited to, n-C3-15 alkylmercaptans such as n-propylmercaptan, n-butylmercaptan, n-amylmercaptan, n-hexylmercaptan, n-heptylmercaptan, n-octylmercaptan, n-nonylmercaptan, n-decylmercaptan, and n-dodecylmercaptan; branched alkylmercaptans such as isopropylmercaptan, isobutylmercaptan, s-butylmercaptan, tert-butylmercaptan, cyclohexylmercaptan, tert-hexadecylmercaptan, tert-laurylmercaptan, tert-nonylmercaptan, tert-octylmercaptan, and tert-tetradecylmercaptan; aromatic ring-containing mercaptans such as allylmercaptan, 3-phenylpropylmercaptan, phenylmercaptan, and mercaptotriphenylmethane. As a skilled artisan understands, the term -mercaptan and -thiol may be used interchangeably to mean C—SH group.

Typical examples of such chain transfer agents also include, but are not limited to, dodecanethiol, butanethiol, isooctyl-3-mercaptopropionate, 2-methyl-5-tert-butyl-thiophenol, carbon tetrachloride, carbon tetrabromide, and the like. Dodecanethiol and carbon tetrabromide are most typically used.

Based on total weight of the monomers to be polymerized, the chain transfer agent may generally be present in an amount from about 0.1% to about 7%, including from about 0.5% to about 6%, and from about 1.0% to about 5%, although it may be present in greater or lesser amounts.

Optional Reactants, Ingredients and Adjuvants

Due to nature of end-use compositions, the ultraviolet-absorbing compounds of this invention may be used with other additives to further enhance the properties of the finished product. Such formulations may be especially preferred in the personal care and performance chemicals fields. These optional ingredients may be incorporated without altering the scope of the current invention, and may be included in order to produce the necessary formulated personal care products.

For example, the composition of the invention also can contain one or more additional cosmetically acceptable additives chosen from conditioning agents, protecting agents, such as, for example, hydrosoluble, antiradical agents, antioxidants, vitamins and pro-vitamins, fixing agents, oxidizing agents, reducing agents, dyes, cleansing agents, anionic, cationic, nonionic and amphoteric surfactants, thickeners, perfumes, pearlizing agents, stabilizers, pH adjusters, filters, preservatives, hydroxy acids, cationic and nonionic polyether associative polyurethanes, polymers other than the cationic polymer described herein, vegetable oils, mineral oils, synthetic oils, polyols such as glycols and glycerol, silicones, aliphatic alcohols, colorants, bleaching agents, highlighting agents and sequestrants. These additives are present in the composition according to the invention in proportions that may range from 0% to 99.99% by weight in relation to the total weight of the composition. The precise amount of each additive may be determined by an expert in the field according to its nature and its function.

It may be especially preferred to formulate the disclosed ultraviolet-absorbing compounds with other UV absorbers, including those that are not covalently bonded into the reaction products of this invention. The addition of these UV absorbers with the ultraviolet-absorbing compounds, especially when the synthesized material is a polymer, may provide any number of benefits, include (without limitation): extended or tailor-made UV spectrum protection, and stabilization of labile UV absorbers, Examples of photolabile UV absorber include, without limitation: avobenzone, para-aminobenzoic acid (PABA) derivatives, cinnamates, and dibenzoyl methane derivatives, all of which degrade over time and reduce UV protection.

UV absorbers that may be formulated with the ultraviolet-absorbing compounds include: octyl salicylate (2-ethylhexyl salicylate, Escalol® 587); pentyl dimethyl PABA; octyl dimethyl PABA (padimate O, Escalol® 507); benzophenone-1; benzophenone-6 (Uvinul® D-49); 2-(2H-benzotriazole-2-yl)-4,6-di-tert-pentylphenol (Uvinul® 3028); ethyl-2-cyano-3,3-diphenylacrylate (Uvinul® 3035); homomenthyl salicylate (homosalate); bis-ethylhexyloxyphenol methoxyphenyl triazine (bemotrizinol, Tinosorb® S); methyl-(1,2,2,6,6-pentamethyl-4-piperidyl)-sebacate (Uvinul® 4092H); benzenepropanoic acid, 3,5-bis(1,1-dimethyl-ethyl)-4-hydroxy-, C7-C9 branched alkyl esters (Irganox® 1135); 2-(2H-benzotriazole-2-yl)-4-methylphenol (Uvinul® 3033P); diethylhexyl butamido triazone (iscotrizinol); amyl dimethyl PABA (lisadimate, glyceryl PABA); 4,6-bis(octylthiomethyl)-o-cresol (Irganox® 1520); CAS number 65447-77-0 (Uvinul® 5062H, Uvinul® 5062GR); red petroleum; ethylhexyl triazone (Uvinul® T-150); octocrylene (Escalol® 597); isoamyl-p-methoxycinnamate (amiloxate, Neo Heliopan® E1000); drometrizole; titanium dioxide; 2,4-di-tert-butyl-6-(5-chloro-2H-benzotriazole-2-yl)-phenol (Uvinul® 3027); 2-hydroxy-4-octyloxybenzophenone (Uvinul® 3008); benzophenone-2 (Uvinul® D-50); diisopropyl methylcinnamate; PEG-25 PABA; 2-(1,1-dimethylethyl)-6-[[3-(1,1-demethylethyl)-2-hydroxy-5-methylphenyl]methyl-4-methylphenyl acrylate (Irganox® 3052); drometrizole trisiloxane (Mexoryl® XL); menthyl anthranilate (meradimate); bis-(1,2,2,6,6-pentamethyl-4-piperidyl)-sebacate; butyl methoxydibenzoylmethane (avobenzone, Escalol® 517); 2-ethoxyethyl p-methoxycinnamate (cinnoxate); benzylidene camphor sulfonic acid (Mexoryl® SL); dimethoxyphenyl-[1-(3,4)]-4,4-dimethyl 1,3-pentanedione; zinc oxide.; N,N'-hexane-1,6-diylbis[3-(3,5-di-tert-butyl-4-hydroxyphenylpropionamide)] (Irganox® 1098); pentaerythritol tetrakis[3-(3,5-di-tert-butyl-4-hydroxyphenyl)propionate] (Irganox® 1010); 2,6-di-tert-butyl-4-[4,6-bis(octylthio)-1,3,5-triazin-2-ylamino]phenol (Irganox® 565); 2-(2H-benzotriazole-2-yl)-4,6-bis(1-methyl-1-phenylethyl) phenol (Uvinul® 3034); trolamine salicylate (triethanolamine salicylate); diethanolamine p-methoxycinnamate (DEA methoxycinnamate); polysilicone-15 (Parsol® SLX); CAS number 152261-33-1 (Uvinul® 5050H); 4-methylbenzylidene camphor (Eusolex® 6300, Parsol® 5000); bisoctrizole (Tinosorb® M); benzenamine, N-phenyl-, reaction products with 2,4,4-trimethylpentene (Irganox® 50507); sulisobenzone, Escalol®577); (2-ethylhexyl)-2-cyano-3,3-diphenylacrylate (Uvinul® 3039); digalloyl trioleate; polyacrylamido methylbenzylidene camphor; glyceryl ethylhexanoate dimethoxycinnamate; 1,3-bis-[(2'-cyano-3',3'-diphenylacryloyl)oxy]-2,2-bis-{[2'-cyano-; bis-(2,2,6,6-tetramethyl-4-piperidyl)-sebacate (Uvinul® 407711); benzophenone-5; 1,3,5-tris(3,5-di-tert-butyl-4-hydroxybenzyl)-1,3,5-triazine-2,4,6(1H,3H,5H)-trione (Irganox® 3114); hexamethylendiamine (Uvinul® 4050H); benzophenone-8 (dioxybenzone); ethyl-4-bis(hydroxypropyl)aminobenzoate(roxadimate); 6-tert-butyl-2-(5-chloro-2H-benzotriazole-2-yl)-4-methylphenol (Uvinul® 3026); p-aminobenzoic acid (PABA); 3,3',3",5,5',5"-hexa-tert-butyl-a-a'-a"-(mesitylene-2,4,6-triyl)tri-p-cresol (Irganox® 1130); lawsone with dihydroxyacetone; benzophenone-9 (Uvinul® DS-49); benzophenone-4; ethylhexyl dimethoxy benzylidene dioxoimidazoline propionate; N,N'-bisformyl-N,N'-bis-(2,2,6,6-tetramethyl-4-piperidinyl)-; 3-benzylidene camphor (Mexoryl® SD); terephthalylidene dicamphor sulfonic acid; camphor benzalkonium methosulfate (Mexoryl® SO); bisdisulizole disodium (Neo Heliopan® AP); etocrylene; ferulic acid; 2-(2H-benzotriazole-2-yl)-4-(1,1,3,3-tetramethylbutyl)-phenol (Uvinul® 3029); 4,6-bis(dodecylthiomethyl)-o-cresol (Irganox® 1726); beta-glucopyranoxy propyl hydroxy benzophenone; phenylbenzimidazole sulfonic acid (ensulizole, Eusolex® 232, Parsol® HS); benzophenone-3 (oxybenzone, Escalol® 567); diethylamine hydroxybenzoyl hexylbenzoate (Uvinul® A Plus); 3',3'-diphenylacryloyl)oxy]methyl}-propane (Uvinul® 3030); and ethylhexyl p-methoxycinnamate (Escalol® 557).

For personal care applications, any known agent that is useful may be included with the ultraviolet-absorbing compounds on the invention. For example, conditioning agents may be added to improve the cosmetic properties of the hair, particularly softness, thickening, untangling, feel, and static electricity and may be in liquid, semi-solid, or solid form such as oils, waxes, or gums. Similarly, any known skin altering agent is useful in the compositions of this invention. Preferred conditioning agents include cationic polymers, cationic surfactants and cationic silicones.

Conditioning agents may be chosen from synthesis oils, mineral oils, vegetable oils, fluorinated or perfluorinated oils, natural or synthetic waxes, silicones, cationic polymers, proteins and hydrolyzed proteins, ceramide type compounds, cationic surfactants, fatty amines, fatty acids and their derivatives, as well as mixtures of these different compounds.

The synthesis oils include polyolefins, e.g., poly-α-olefins such as polybutenes, polyisobutenes and polydecenes. The polyolefins can be hydrogenated.

The mineral oils suitable for use in the compositions of the invention include hexadecane and oil of paraffin.

A list of suitable animal and vegetable oils comprises sunflower, corn, soy, avocado, jojoba, squash, raisin seed, sesame seed, walnut oils, fish oils, glycerol tricaprocaprylate, Purcellin oil or liquid jojoba, and blends thereof.

Suitable natural or synthetic oils include eucalyptus, lavender, vetiver, litsea cubeba, lemon, sandalwood, rosemary, chamomile, savory, nutmeg, cinnamon, hyssop, caraway, orange, geranium, cade, and bergamot.

Suitable natural and synthetic waxes include carnauba wax, candelila wax, alfa wax, paraffin wax, ozokerite wax, vegetable waxes such as olive wax, rice wax, hydrogenated jojoba wax, absolute flower waxes such as black currant flower wax, animal waxes such as bees wax, modified bees wax (cerabellina), marine waxes and polyolefin waxes such as polyethylene wax, and blends thereof.

The cationic polymers that may be used as a conditioning agent according to the invention are those known to improve the cosmetic properties of hair treated by detergent compositions. The expression "cationic polymer" as used herein, indicates any polymer containing cationic groups and/or ionizable groups in cationic groups. The cationic polymers used generally have a molecular weight the average number of which falls between about 500 g/mol and 5,000,000 g/mol and preferably between 1000 g/mol and 3,000,000 g/mol.

The preferred cationic polymers are chosen from among those containing units including primary, secondary, tertiary, and/or quaternary amine groups that may either form part of the main polymer chain or a side chain.

Useful cationic polymers include known polyamine, polyaminoamide, and quaternary polyammonium types of polymers, such as:
(1) homopolymers and copolymers derived from acrylic or methacrylic esters or amides. The copolymers can contain one or more units derived from acrylamides, methacrylamides, diacetone acrylamides, acrylamides and methacrylamides, acrylic or methacrylic acids or their esters, vinyllactams such as vinyl pyrrolidone or vinyl caprolactam, and vinyl esters. Specific examples include: copolymers of acrylamide and dimethyl amino ethyl methacrylate quaternized with dimethyl sulfate or with an alkyl halide; copolymers of acrylamide and methacryloyl oxyethyl trimethyl ammonium chloride; the copolymer of acrylamide and methacryloyl oxyethyl trimethyl ammonium methosulfate; copolymers of vinyl pyrrolidone/dialkylaminoalkyl acrylate or methacrylate, optionally quaternized, such as the products sold under the name Gafquat® by International Specialty Products; the dimethyl amino ethyl methacrylate/vinyl caprolactam/vinyl pyrrolidone terpolymers, such as the product sold under the name Gaffix® VC 713 by International Specialty Products; the vinyl pyrrolidone/methacrylamidopropyl dimethylamine copolymer, marketed under the name Styleze® CC 10 by International Specialty Products; and the vinyl pyrrolidone/quaternized dimethyl amino propyl methacrylamide copolymers such as the product sold under the name Gafquat® HS 100 by International Specialty Products (Wayne, N.J.).
(2) Derivatives of cellulose ethers containing quaternary ammonium groups, such as hydroxy ethyl cellulose quaternary ammonium that has reacted with an epoxide substituted by a trimethyl ammonium group.
(3) Derivatives of cationic cellulose such as cellulose copolymers or derivatives of cellulose grafted with a hydrosoluble quaternary ammonium monomer, as described in U.S. Pat. No. 4,131,576, such as the hydroxy alkyl cellulose, and the hydroxymethyl-, hydroxyethyl- or hydroxypropyl-cellulose grafted with a salt of methacryloyl ethyl trimethyl ammonium, methacrylamidopropyl trimethyl ammonium, or dimethyl diallyl ammonium.
(4) Cationic polysaccharides such as described in U.S. Pat. Nos. 3,589,578 and 4,031,307, guar gums containing cationic trialkyl ammonium groups and guar gums modified by a salt, e.g., chloride of 2,3-epoxy propyl trimethyl ammonium.
(5) Polymers composed of piperazinyl units and alkylene or hydroxy alkylene divalent radicals with straight or branched chains, possibly interrupted by atoms of oxygen, sulfur, nitrogen, or by aromatic or heterocyclic cycles, as well as the products of the oxidation and/or quaternization of such polymers.
(6) Water-soluble polyamino amides prepared by polycondensation of an acid compound with a polyamine. These polyamino amides may be reticulated.
(7) Derivatives of polyamino amides resulting from the condensation of polyalcoylene polyamines with polycarboxylic acids followed by alcoylation by bi-functional agents.
(8) Polymers obtained by reaction of a polyalkylene polyamine containing two primary amine groups and at least one secondary amine group with a dioxycarboxylic acid chosen from among diglycolic acid and saturated dicarboxylic aliphatic acids having 3 to 8 atoms of carbon. Such polymers are described in U.S. Pat. Nos. 3,227,615 and 2,961,347.
(9) Cyclopolymers of alkyl dialyl amine or dialkyl diallyl ammonium such as the homopolymer of dimethyl diallyl ammonium chloride and copolymers of diallyl dimethyl ammonium chloride and acrylamide.
(10) Quaternary diammonium polymers such as hexadimethrine chloride.
(11) Quaternary polyammonium polymers, including, for example, Mirapol® A 15, Mirapol® AD1, Mirapol® AZ1, and Mirapol® 175 products sold by Miranol.
(12) Quaternary polymers of vinyl pyrrolidone and vinyl imidazole such as the products sold under the names Luviquat® FC 905, FC 550, and FC 370 by BASF Corp. (Ludwigshafen, DE).
(13) Quaternary polyamines.
(14) Reticulated polymers known in the art.

Other cationic polymers that may be used within the context of the invention are cationic proteins or hydrolyzed cationic proteins, polyalkyleneimines such as polyethyleneimines, polymers containing vinyl pyridine or vinyl pyridinium units, condensates of polyamines and epichlorhydrins, quaternary polyurethanes, and derivatives of chitin.

Preferred cationic polymers are derivatives of quaternary cellulose ethers, the homopolymers and copolymers of dimethyl diallyl ammonium chloride, quaternary polymers of vinyl pyrrolidone and vinyl imidazole, and mixtures thereof.

The conditioning agent can be any silicone known by those skilled in the art to be useful as a conditioning agent. The silicones suitable for use according to the invention include polyorganosiloxanes that are insoluble in the composition. The silicones may be present in the form of oils, waxes, resins, or gums. They may be volatile or non-volatile. The silicones can be selected from polyalkyl siloxanes, polyaryl siloxanes, polyalkyl aryl siloxanes, silicone gums and resins, and polyorgano siloxanes modified by organofunctional groups, and mixtures thereof.

Suitable polyalkyl siloxanes include polydimethyl siloxanes with terminal trimethyl silyl groups or terminal dimethyl silanol groups (dimethiconol) and polyalkyl (C1-C20) siloxanes.

Suitable polyalkyl aryl siloxanes include polydimethyl methyl phenyl siloxanes and polydimethyl diphenyl siloxanes, linear or branched.

The silicone gums suitable for use herein include polydiorganosiloxanes preferably having a number-average molecular weight between 200,000 g/mol and 1,000,000, g/mol used alone or mixed with a solvent. Examples include polymethyl siloxane, polydimethyl siloxane/methyl vinyl siloxane gums, polydimethyl siloxane/diphenyl siloxane, polydimethyl siloxane/phenyl methyl siloxane and polydimethyl siloxane/diphenyl siloxane/methyl vinyl siloxane.

Suitable silicone resins include silicones with a dimethyl/trimethyl siloxane structure and resins of the trimethyl siloxy-silicate type.

The organo-modified silicones suitable for use in the invention include silicones such as those previously defined and containing one or more organofunctional groups attached by means of a hydrocarbon radical and grafted siliconated polymers. Particularly preferred are amino functional silicones.

The silicones may be used in the form of emulsions, nano-emulsions, or micro-emulsions.

The conditioning agent can be a protein or hydrolyzed cationic or non-cationic protein. Examples of these compounds include hydrolyzed collagens having triethyl ammonium groups, hydrolyzed collagens having trimethyl ammonium and trimethyl stearyl ammonium chloride groups, hydrolyzed animal proteins having trimethyl benzyl ammonium groups (benzyltrimonium hydrolyzed animal protein), hydrolyzed proteins having groups of quaternary ammonium on the polypeptide chain, including at least one C1-C18 alkyl.

Hydrolyzed proteins include Croquat L, in which the quaternary ammonium groups include a C12 alkyl group, Croquat M, in which the quaternary ammonium groups include C10-C18 alkyl groups, Croquat S in which the quaternary ammonium groups include a C18 alkyl group and Crotein Q in which the quaternary ammonium groups include at least one C1-C18 alkyl group. These products are sold by Croda.

The conditioning agent can comprise quaternized vegetable proteins such as wheat, corn, or soy proteins such as cocodimonium hydrolyzed wheat protein, laurdimonium hydrolyzed wheat protein and steardimonium hydrolyzed wheat protein, 2-N-stearoyl amino-octadecane-1,3-diol, 2-N-behenoyl amino-octadecane-1,3-diol, 2-N-[2-hydroxypalmitoyl]-amino-octadecane-1,3-diol, 2-N-stearoyl amino-octadecane-1,3,4-triol, N-stearoyl phytosphingosine, 2-N-palmitoyl amino-hexadecane-1,3-diol, bis-(N-hydroxy ethyl N-cetyl)malonamide, N-(2-hydroxy ethyl)-N-(3-cetoxyl-2-hydroxy propyl) amide of cetylic acid, N-docosanoyl N-methyl-D-glucamine and mixtures of such compounds.

The conditioning agent can be a cationic surfactant such as a salt of a primary, secondary, or tertiary fatty amine, optionally polyoxyalkylenated, a quaternary ammonium salt, a derivative of imadazoline, or an amine oxide. Suitable examples include mono-, di-, or tri-alkyl quaternary ammonium compounds with a counterion such as a chloride, methosulfate, tosylate, etc. including, but not limited to, cetrimonium chloride, dicetyldimonium chloride, behentrimonium methosulfate, and the like. The presence of a quaternary ammonium compound in conjunction with the polymer described above reduces static and enhances combing of hair in the dry state. The polymer also enhances the deposition of the quaternary ammonium compound onto the hair substrate thus enhancing the conditioning effect of hair.

The conditioning agent can be any fatty amine known to be useful as a conditioning agent; e.g. dodecyl, cetyl or stearyl amines, such as stearamidopropyl dimethylamine.

The conditioning agent can be a fatty acid or derivatives thereof known to be useful as conditioning agents. Suitable fatty acids include myristic acid, palmitic acid, stearic acid, behenic acid, oleic acid, linoleic acid, and isostearic acid. The derivatives of fatty acids include carboxylic ester acids including mono-, di-, tri- and tetra-carboxylic acids.

The conditioning agent can be a fluorinated or perfluorinated oil. The fluoridated oils may also be fluorocarbons such as fluoramines, e.g., perfluorotributylamine, fluoridated hydrocarbons, such as perfluorodecahydronaphthalene, fluoroesters, and fluoroethers.

Of course, mixtures of two or more conditioning agents can be used.

The conditioning agent or agents can be present in an amount of 0.001% to 20%, preferably from 0.01% to 10%, and even more preferably from 0.1% to 3% by weight based on the total weight of the final composition.

The composition of the invention can contain one or more protecting agents to prevent or limit the degrading effects of natural physical and/or chemical assaults on the keratinous materials.

The antioxidants or antiradical agents can be selected from phenols such as BHA (tert-butyl-4-hydroxy anisole), BHT (2,6-di-tert-butyl-p-cresol), TBHQ (tert-butyl hydroquinone), polyphenols such as proanthocyanodic oligomers, flavonoids, hindered amines such as tetra amino piperidine, erythorbic acid, polyamines such as spermine, cysteine, glutathione, superoxide dismutase, and lactoferrin.

The vitamins can be selected from ascorbic acid (vitamin C), vitamin E, vitamin E acetate, vitamin E phosphate, B vitamins such as B3 and B5, vitamin PP (i.e., niacin), vitamin A, and derivatives thereof. The provitamins can be selected from panthenol and retinol.

The protecting agent can be present in an amount 0.001% to 20% by weight, preferably from 0.01% to 10% by weight, and more preferably 0.1 to 5% by weight of the total weight of the final composition.

In addition, the compositions according to the invention advantageously include at least one surfactant, which can be present in an amount of 0.1% and 60% preferably 1% and 40%, and more preferably 5% and 30% by weight based on the total weight of the composition. The surfactant may be chosen from among anionic, amphoteric, or non-ionic surfactants, or mixtures of them known to be useful in personal care compositions.

Additional thickeners or viscosity increasing agents may be included in the composition of the invention, such as: Acetamide MEA; acrylamide/ethalkonium chloride acrylate copolymer; acrylamide/ethyltrimonium chloride acrylate/ethalkonium chloride acrylate copolymer; acrylamides copolymer; acrylamide/sodium acrylate copolymer; acrylamide/sodium acryloyldimethyltaurate copolymer; acrylates/acetoacetoxyethyl methacrylate copolymer; acrylates/beheneth-25 methacrylate copolymer; acrylates/C10-C30 alkyl acrylate crosspolymer; acrylates/ceteth-20 itaconate copolymer; acrylates/ceteth-20 methacrylate copolymer; acrylates/laureth-25 methacrylate copolymer; acrylates/palmeth-25 acrylate copolymer; acrylates/palmeth-25 itaconate copolymer; acrylates/steareth-50 acrylate copolymer; acrylates/steareth-20 itaconate copolymer; acrylates/steareth-20 methacrylate copolymer; acrylates/stearyl methacrylate copolymer; acrylates/vinyl isodecanoate crosspolymer; acrylic acid/acrylonitrogens copolymer; adipic acid/methyl DEA crosspolymer; agar; agarose; alcaligenes polysaccharides; algin; alginic acid; almondamide DEA; almondamidopropyl betaine; aluminum/magnesium hydroxide stearate; ammonium acrylates/acrylonitrogens copolymer; ammonium acrylates copolymer; ammonium acryloyldimethyltaurate/vinyl formamide copolymer; ammonium acryloyldimethyltaurate/VP copolymer; ammonium alginate; ammonium chloride; ammonium polyacryloyldimethyl taurate; ammonium sulfate; amylopectin; apricotamide DEA; apricotamidopropyl betaine; arachidyl alcohol; arachidyl glycol; arachis hypogaea (peanut) flour; ascorbyl methylsilanol pectinate; astragalus gummifer gum; attapulgite; avena sativa (oat) kernel flour; avocadamide DEA; avocadamidopropyl betaine; azelamide MEA; babassuamide DEA; babassuamide MEA; babassuamidopropyl betaine; behenamide DEA; behenamide MEA; behenamidopropyl betaine; behenyl betaine; bentonite; butoxy chitosan; caesalpinia spinosa gum; calcium alginate; calcium carboxymethyl cellulose; calcium carrageenan; calcium chloride; calcium potassium carbomer; calcium starch octenylsuccinate; C20-40 alkyl stearate; canolamidopropyl betaine; capramide DEA; capryl/capramidopropyl betaine; carbomer; carboxybutyl chitosan; carboxymethyl cellulose acetate butyrate; carboxymethyl chitin; carboxymethyl chitosan; carboxymethyl dextran; carboxymethyl hydroxyethylcellulose; carboxymethyl hydroxypropyl guar; carnitine; cellulose acetate propionate carboxylate; cellulose gum; ceratonia siliqua gum; cetearyl alcohol; cetyl alcohol; cetyl babassuate; cetyl betaine; cetyl glycol; cetyl hydroxyethylcellulose; chimyl alcohol; cholesterol/HDI/pullulan copolymer; cholesteryl hexyl dicarbamate pullulan; citrus aurantium dulcis (orange) peel extract; cocamide DEA; cocamide MEA; cocamide MIPA; cocamidoethyl betaine; cocamidopropyl betaine; cocamidopropyl hydroxysultaine; coco-betaine; coco-hydroxysultaine; coconut alcohol; coco/oleamidopropyl betaine; coco-Sultaine; cocoyl sarcosinamide DEA; cornamide/cocamide DEA; cornamide DEA; croscarmellose; crosslinked bacillus/glucose/sodium glutamate ferment; cyamopsis tetragonoloba (guar) gum; decyl alcohol; decyl betaine; dehydroxanthan gum; dextrin;

dibenzylidene sorbitol; diethanolaminooleamide DEA; diglycol/CHDM/isophthalates/STP copolymer; dihydroabietyl behenate; dihydrogenated tallow benzylmonium hectorite; dihydroxyaluminum aminoacetate; dimethicone/PEG-10 crosspolymer; dimethicone/PEG-15 crosspolymer; dimethicone propyl PG-betaine; dimethylacrylamide/acrylic acid/polystyrene ethyl methacrylate copolymer; dimethylacrylamide/sodium acryloyldimethyltaurate crosspolymer; disteareth-100 IPDI; DMAPA acrylates/acrylic acid/acrylonitrogens copolymer; erucamidopropyl hydroxysultaine; ethylene/sodium acrylate copolymer; gelatin; gellan gum; glyceryl alginate; glycine soja (soybean) flour; guar hydroxypropyltrimonium chloride; hectorite; hyaluronic acid; hydrated silica; hydrogenated potato starch; hydrogenated tallow; hydrogenated tallowamide DEA; hydrogenated tallow betaine; hydroxybutyl methylcellulose; hydroxyethyl acrylate/sodium acryloyldimethyl taurate copolymer; hydroxyethylcellulose; hydroxyethyl chitosan; hydroxyethyl ethylcellulose; hydroxyethyl stearamide-MIPA; hydroxylauryl/hydroxymyristyl betaine; hydroxypropylcellulose; hydroxypropyl chitosan; hydroxypropyl ethylenediamine carbomer; hydroxypropyl guar; hydroxypropyl methylcellulose; hydroxypropyl methylcellulose stearoxy ether; hydroxypropyl starch; hydroxypropyl starch phosphate; hydroxypropyl xanthan gum; hydroxystearamide MEA; isobutylene/sodium maleate copolymer; isostearamide DEA; isostearamide MEA; isostearamide mIPA; isostearamidopropyl betaine; lactamide MEA; lanolinamide DEA; lauramide DEA; lauramide MEA; lauramide MIPA; lauramide/myristamide DEA; lauramidopropyl betaine; lauramidopropyl hydroxysultaine; laurimino bispropanediol; lauryl alcohol; lauryl betaine; lauryl hydroxysultaine; lauryl/myristyl glycol hydroxypropyl ether; lauryl sultaine; lecithinamide DEA; linoleamide DEA; linoleamide MEA; linoleamide MIPA; lithium magnesium silicate; lithium magnesium sodium silicate; macro cystis pyrifera (kelp); magnesium alginate; magnesium/aluminum/hydroxide/carbonate; magnesium aluminum silicate; magnesium silicate; magnesium trisilicate; methoxy PEG-22/dodecyl glycol copolymer; methylcellulose; methyl ethylcellulose; methyl hydroxyethylcellulose; microcrystalline cellulose; milkamidopropyl betaine; minkamide DEA; minkamidopropyl betaine; MIPA-myristate; montmorillonite; Moroccan lava clay; myristamide DEA; myristamide MEA; myristamide MIPA; myristamidopropyl betaine; myristamidopropyl hydroxysultaine; myristyl alcohol; myristyl betaine; natto gum; nonoxynyl hydroxyethylcellulose; oatamide MEA; oatamidopropyl betaine; octacosanyl glycol isostearate; octadecene/MA copolymer; oleamide DEA; oleamide MEA; oleamide MIPA; oleamidopropyl betaine; oleamidopropyl hydroxysultaine; oleyl betaine; olivamide DEA; olivamidopropyl betaine; oliveamide MEA; palmamide DEA; palmamide MEA; palmamide MIPA; palmamidopropyl betaine; palmitamide DEA; palmitamide MEA; palmitamidopropyl betaine; palm kernel alcohol; palm kernelamide DEA; palm kernelamide MEA; palm kernelamide MIPA; palm kernelamidopropyl betaine; peanutamide MEA; peanutamide MIPA; pectin; PEG-800; PEG-crosspolymer; PEG-150/decyl alcohol/SMDI copolymer; PEG-175 diisostearate; PEG-190 distearate; PEG-15 glyceryl tristearate; PEG-140 glyceryl tristearate; PEG-240/HDI copolymer bis-decyltetradeceth-20 ether; PEG-100/IPDI copolymer; PEG-180/laureth-50/TMMG copolymer; PEG-10/lauryl dimethicone crosspolymer; PEG-15/lauryl dimethicone crosspolymer; PEG-2M; PEG-5M; PEG-7M; PEG-9M; PEG-14M; PEG-20M; PEG-23M; PEG-25M; PEG-45M; PEG-65M; PEG-90M; PEG-115M; PEG-160M; PEG-180M; PEG-120 methyl glucose trioleate; PEG-180/octoxynol-40/TMMG copolymer; PEG-150 pentaerythrityl tetrastearate; PEG-4 rapeseedamide; PEG-150/stearyl alcohol/SMDI copolymer; phaseolus angularis seed powder; polianthes tuberosa extract; polyacrylate-3; polyacrylic acid; polycyclopentadiene; polyether-1; polyethylene/isopropyl maleate/MA copolyol; polyglyceryl-3 disiloxane dimethicone; polyglyceryl-3 polydimethylsiloxyethyl dimethicone; polymethacrylic acid; polyquaternium-52; polyvinyl alcohol; potassium alginate; potassium aluminum polyacrylate; potassium carbomer; potassium carrageenan; potassium chloride; potassium palmate; potassium polyacrylate; potassium sulfate; potato starch modified; PPG-2 cocamide; PPG-1 hydroxyethyl caprylamide; PPG-2 hydroxyethyl cocamide; PPG-2 hydroxyethyl coco/isostearamide; PPG-3 hydroxyethyl soyamide; PPG-14 laureth-60 hexyl dicarbamate; PPG-14 laureth-60 isophoryl dicarbamate; PPG-14 palmeth-60 hexyl dicarbamate; propylene glycol alginate; PVP/decene copolymer; PVP montmorillonite; pyres cydonia seed; pyrus malus (apple) fiber; rhizobian gum; ricebranamide DEA; ricinoleamide DEA; ricinoleamide MEA; ricinoleamide MIPA; ricinoleamidopropyl betaine; ricinoleic acid/adipic acid/AEEA copolymer; rosa multiflora flower wax; sclerotium gum; sesamide DEA; sesamidopropyl betaine; sodium acrylate/acryloyldimethyl taurate copolymer; sodium acrylates/acrolein copolymer; sodium acrylates/acrylonitrogens copolymer; sodium acrylates copolymer; sodium acrylates crosspolymer; sodium acrylate/sodium acrylamidomethylpropane sulfonate copolymer; sodium acrylates/vinyl isodecanoate crosspolymer; sodium acrylate/vinyl alcohol copolymer; sodium carbomer; sodium carboxymethyl chitin; sodium carboxymethyl dextran; sodium carboxymethyl beta-glucan; sodium carboxymethyl starch; sodium carrageenan; sodium cellulose sulfate; sodium chloride; sodium cyclodextrin sulfate; sodium hydroxypropyl starch phosphate; sodium isooctylene/MA copolymer; sodium magnesium fluorosilicate; sodium oleate; sodium palmitate; sodium palm kernelate; sodium polyacrylate; sodium polyacrylate starch; sodium polyacryloyldimethyl taurate; sodium polygamma-glutamate; sodium polymethacrylate; sodium polystyrene sulfonate; sodium silicoaluminate; sodium starch octenylsuccinate; sodium stearate; sodium stearoxy PG-hydroxyethylcellulose sulfonate; sodium styrene/acrylates copolymer; sodium sulfate; sodium tallowate; sodium tauride acrylates/acrylic acid/acrylonitrogens copolymer; sodium tocopheryl phosphate; solanum tuberosum (potato) starch; soyamide DEA; soyamidopropyl betaine; starch/acrylates/acrylamide copolymer; starch hydroxypropyltrimonium chloride; stearamide AMP; stearamide DEA; stearamide DEA-distearate; stearamide DIBA-stearate; stearamide MEA; stearamide MEA-stearate; stearamide MIPA; stearamidopropyl betaine; steareth-60 cetyl ether; steareth-100/PEG-136/HDI copolymer; stearyl alcohol; stearyl betaine; sterculia urens gum; synthetic fluorphlogopite; tallamide DEA; tallow alcohol; tallowamide DEA; tallowamide MEA; tallowamidopropyl betaine; tallowamidopropyl hydroxysultaine; tallowamine oxide; tallow betaine; tallow dihydroxyethyl betaine; tamarindus indica seed gum; tapioca starch; TEA-alginate; TEA-carbomer; TEA-hydrochloride; trideceth-2 carboxamide MEA; tridecyl alcohol; triethylene glycol dibenzoate; trimethyl pentanol hydroxyethyl ether; triticum vulgare (wheat) germ powder; triticum vulgare (wheat) kernel flour; triticum vulgare (wheat) starch; tromethamine acrylates/acrylonitrogens copolymer; tromethamine magnesium aluminum silicate; undecyl alcohol; undecylenamide DEA; undecylenamide MEA; undecylenamidopropyl betaine; welan gum; wheat germamide DEA; wheat germamidopropyl betaine; xanthan gum; yeast beta-glucan; yeast polysaccharides and zea mays (corn) starch.

Preferred thickeners or viscosity increasing agents include carbomer, aculyn and Stabileze®, e.g. crosslinked acrylic acid, crosslinked poly(methylvinyl ether/maleic anhydride) copolymer, acrylamides, carboxymethyl cellulose and the like.

The compositions according to the invention may be used to wash and treat keratinous material such as hair, skin, eyelashes, eyebrows, fingernails, lips, and hairy skin.

The compositions according to the invention may also take the form of after-shampoo compositions, to be rinsed off or not, for permanents, straightening, waving, dyeing, or bleaching, or the form of rinse compositions to be applied before or after dyeing, bleaching, permanents, straightening, relaxing, waving or even between the two stages of a permanent or straightening process.

The compositions of the invention may also take the form of skin-washing compositions, and particularly in the form of solutions or gels for the bath or shower, or of make-up removal products.

The compositions of the invention may also be in the form of aqueous or hydro-alcoholic solutions for skin and/or hair care.

The compositions according to the invention can be detergent compositions such as shampoos, bath gels, and bubble baths. In this embodiment, the compositions will comprise a generally aqueous washing base. The surfactant or surfactants that form the washing base may be chosen alone or in blends, from known anionic, amphoteric, or non-ionic surfactants. The quantity and quality of the washing base must be sufficient to impart a satisfactory foaming and/or detergent value to the final composition. The washing base can be from 4% to 50% by weight, preferably from 6% to 35% by weight, and even more preferentially from 8% to 25% by weight of the total weight of the final composition.

With respect to personal care products, additional formulation ingredients of particular interest are those selected from the list comprising: anti-oxidants, bronzing/self-tanning agents, colorants, defoamers, emollients, fragrances, humectants, insect repellants, lower monoalcohols, lower polyols, micro- and nano-particulate UV absorbants, moisturizers, pigments, preservatives, propellants, oils, surfactants, thickeners, water, and waxes.

With respect to coatings, packaging, plastics, and/or printing product, additional formulation ingredients of particular interest are selected from the list comprising: colorants, defoamers, dyes, fragrances, lacquers, lakes, latexes, micro- and nano-particulate UV absorbents, pigments, plasticizers, preservatives (including biocides), solvents, surfactants, thickeners, varnishes, and water.

Product Forms

The ultraviolet-absorbing compounds of the invention may take any form. Without limitation, the synthesized ultraviolet-absorbing compounds may exist in solution, emulsion, microemulsion, latex, precipitated particles, powder, or precipitated rubber. The synthesized product also may be purified, meaning that one or more reactant(s), solvent(s), side product(s), and/or degradation product(s) are removed by methods known to one skilled in the art.

Due in part to the selected reactants, synthesis method, optional post-processing steps, and end use, the synthesized ultraviolet-absorbing compounds of this invention may assume a wide variety of forms. For example, the ultraviolet-absorbing compounds may be dried to produce a solid or solid-like products, including, without restriction: beads, filaments, films, foams, granules, powders, sheets, threads, and/or powders. In some eases it may be desirable to present the synthesized product as an emulsion, foam, latex, or solution.

As described earlier, it will be appreciated that the ultraviolet-absorbing compounds of the invention may find greatest use in a formulation with one or more ingredients. Cosmetic compositions according to the invention may, for example, be used as care and/or sun protection product for the face and/or the body having a consistency ranging from liquid to semi-liquid (e.g., milks, creams), and gels, creams, pastes, powders (including compacted powders), and wax-like compositions (e.g., lip balms).

Due to the great potential for controlling the reactants, the product may comprise from about 0.01% to about 100% of the described ultraviolet-absorbing compound.

For compositions intended to protect the hair from UV radiation, suitable product forms include, but not limited to: conditioners, dispersions, emulsions, gels, lotions, mists, mousses, shampoos, and sprays.

Optionally, formulations comprising the invention may be packaged as an aerosol and may be provided in the form of a mousse, spray, or mist. It may be advantageous to utilize propellants (e.g., hydrofluorinated compounds dichlorodifluoromethane, difluoroethane, dimethyl ether, isobutene, n-butane, propane, trichlorofluoromethane) to aide in their delivery.

In a different embodiment, compositions of this invention may be provided in the form of vaporizable fluid lotions to be applied to the skin or the hair. Pressurized devices are a suitable means for vaporizing fluid lotions, and are known to one skilled in the art. For example, they are described in U.S. Pat. Nos. 4,077,441 and 4,850,517.

Characterizing the Reaction Product

The ultraviolet-absorbing compounds can be analyzed by known techniques to characterize the product. Especially preferred are the techniques of $^{13}C$ nuclear magnetic resonance (NMR) spectroscopy, gas chromatography (GC), and gel permeation chromatography (GPC) in order to decipher polymer identity, residual UV absorber concentrations, polymer molecular weight, and polymer molecular weight distribution.

Nuclear magnetic resonance (NMR) spectroscopy is an especially preferred method to probe the polymerization product in terms of chemical properties such as monomeric composition, sequencing and tacticity. Analytical equipment suitable for these analyses include the Inova 400-MR NMR System by Varian Inc. (Palo Alto, Calif.). References broadly describing NMR include: Yoder, C. H. and Schaeffer Jr., C. D., *Introduction to Multinuclear NMR*, The Benjamin/Cummings Publishing Company, Inc., 1987; and Silverstein, R. M., et al., *Spectrometric Identification of Organic Compounds*, John Wiley & Sons, 1981, which are incorporated in their entirety by reference.

Residual monomer levels can be measured by GC, which can be used to indicate the extent of reactant conversion by the polymerization process. GC analytical equipment to perform these tests are commercially available, and include the following units: Series 5880, 5890, and 6890 GC-FID and GC-TCD by Agilent Technologies, Inc. (Santa Clara, Calif.). GC principles are described in *Embodiment Practice of Gas Chromatography*, third edition (John Wiley & Sons, 1995) by Robert L. Grob and Eugene F. Barry, which is hereby incorporated in its entirety by reference.

GPC is an analytical method that separates molecules based on their hydrodynamic volume (or size) in solution of the mobile phase, such as hydroalcoholic solutions with surfactants. GPC is a preferred method for measuring polymer molecular weight distributions. This technique can be performed on known analytical equipment sold for this purpose, and include the TDAmax™ Elevated Temperature GPC System and the RImax™ Conventional Calibration System by Viscotek™ Corp. (Houston, Tex.). In addition, GPC employs analytical standards as a reference, of which a plurality of narrow-distribution polyethylene glycol and polyethylene oxide standards representing a wide range in molecular weight is the preferred. These analytical standards are available for purchase from Rohm & Haas Company (Philadelphia, Pa.) and Varian Inc. (Palo Alto, Calif.). GPC is described in the following texts, which are hereby incorporated in their entirety by reference: Schroder, E., et al., *Polymer Characterization*, Hanser Publishers, 1989; Billingham, N.C., *Molar Mass Measurements in Polymer Science*, Halsted Press, 1979; and Billmeyer, F., *Textbook of Polymer Science*, Wiley Interscience, 1984.

The invention will now be described with reference to the following examples:

EXAMPLES

Example 1

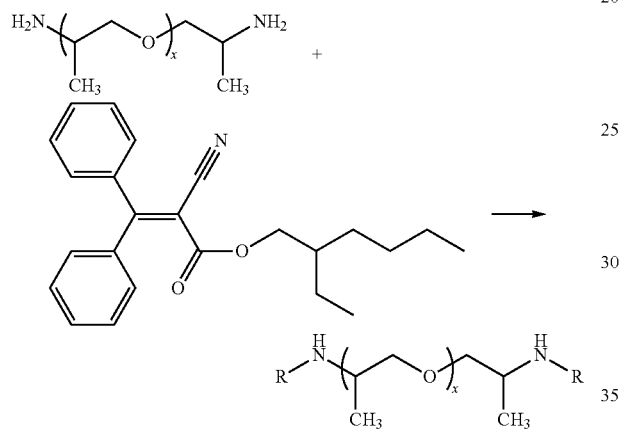

wherein R=

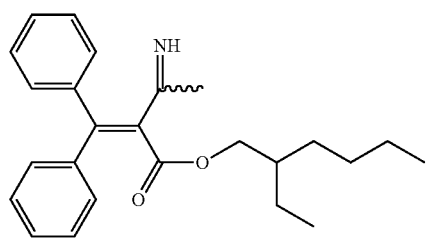

A diamine-terminated polypropylene glycol having an approximate molecular weight of 2,000 g/mol (Jeffamine® D2000, Huntsman Corporation) (100 g) and octocrylene (Escalol® 597, International Specialty Products) (30 g) were charged into a 0.5 L, four-necked resin kettle equipped with an anchor agitator, a thermocouple, a condenser, and a nitrogen surface purge adaptor.

The agitator was turned on to 200 rpm and the mixture was heated to 100° C. in 30 minutes. During the entire reaction, nitrogen was purged through the reacting mixture. Once the temperature reached 100° C., the kettle was maintained isothermally for 1 hour. Then, the temperature was increased to 180° C. within 30 minutes, and the kettle was held at this higher temperature for 5 hours. A vacuum was pulled for the final 4 hours to remove the excess volatile materials.

The synthesized polymer has a theoretical molar ratio of 1.2 effective amine units:1 UV absorber.

Example 2

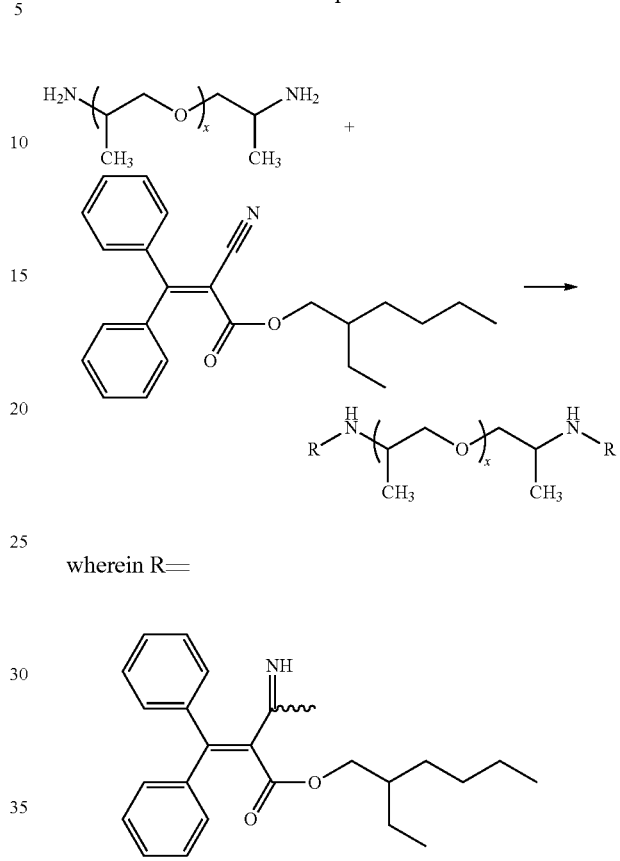

wherein R=

A diamine-terminated polypropylene glycol having an approximate molecular weight of 2,000 g/mol (Jeffamine® D2000, Huntsman Corporation) (100 g) and octocrylene (Escalol® 597, International Specialty Products) (22 g) were charged into a 0.5 L, four-necked resin kettle equipped with an anchor agitator, a thermocouple, a condenser, and a nitrogen surface purge adaptor.

The agitator was turned on to 200 rpm and the mixture was heated to 180° C. in 45 minutes. During the entire reaction, nitrogen was purged through the reacting mixture. Once the temperature reached 180° C., the kettle was maintained isothermally for 15 hours. A vacuum was pulled for the final 4 hours to remove the excess volatile materials.

The synthesized polymer has a theoretical molar ratio of 1.6 effective amine units:1 UV absorber.

Example 3

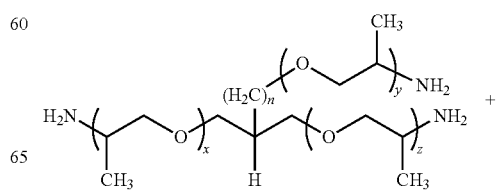

-continued

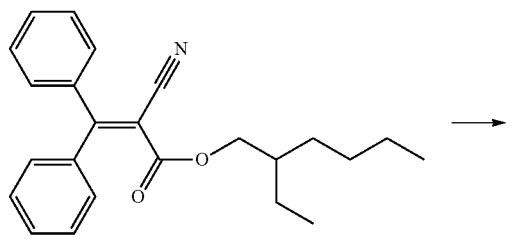

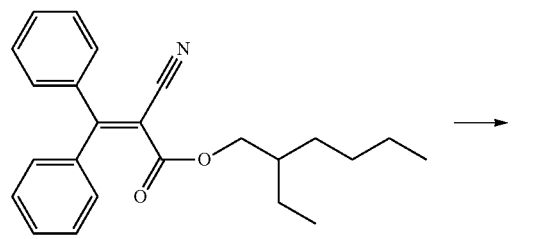

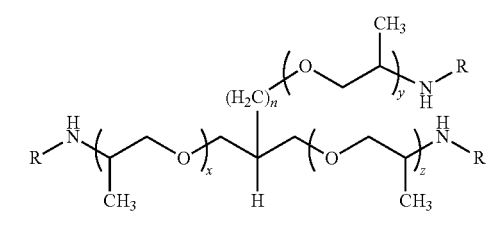

wherein R=

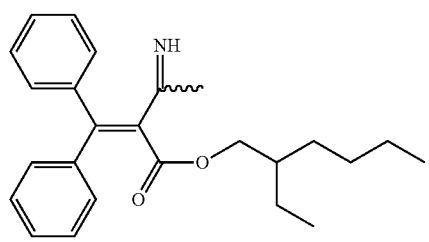

wherein R=

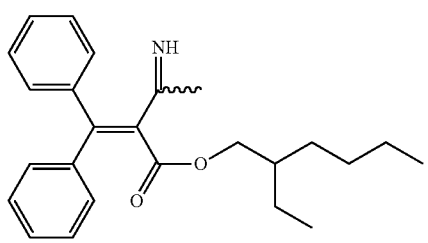

A triamine-terminated polypropylene glycol having an approximate molecular weight of 3000 g/mol (Jeffamine® D3000, Huntsman Corporation) (100 g), octocrylene (Escalol® 597, International Specialty Products) (35 g), and the antioxidant 2,6-di-tert-butyl-p-cresol (BHT) (0.5 g) were charged into a 0.5 L, four-necked resin kettle equipped with an anchor agitator, a thermocouple, a condenser, and a nitrogen surface purge adaptor.

The agitator was turned on to 200 rpm and the mixture was heated to 180° C. in 60 minutes. During the entire reaction, nitrogen was purged through the reacting mixture. Once the temperature reached 180° C., the kettle was maintained isothermally for 7 hours. A vacuum was pulled for the final 4 hours to remove the excess volatile materials.

The synthesized polymer has a theoretical molar ratio of 1.0 effective amine units:1 UV absorber.

Example 4

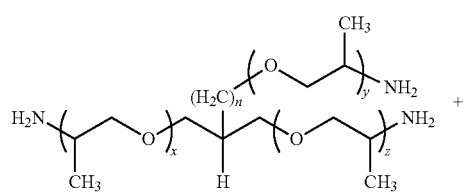

A triamine-terminated polypropylene glycol having an approximate molecular weight of 440 g/mol (Jeffamine T403, Huntsman Corporation) (200 g) and octocrylene (Escalol® 597, International Specialty Products) (552 g) were charged into 0.5 L, four-necked resin kettle equipped with an anchor agitator, a thermocouple, a condenser, and a nitrogen surface purge adaptor.

The agitator was turned on to 200 rpm and the mixture was heated to 180° C. in 60 minutes. During the entire reaction, nitrogen was purged through the reacting mixture. Once the temperature reached 180° C., the kettle was maintained isothermally for 7 hours. A vacuum was pulled for the final 8 hours to remove the excess volatile materials.

The synthesized polymer has a theoretical molar ratio of 0.89 effective amine units:1 UV absorber.

Example 5

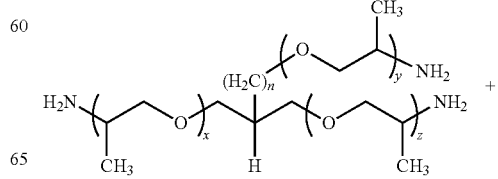

-continued

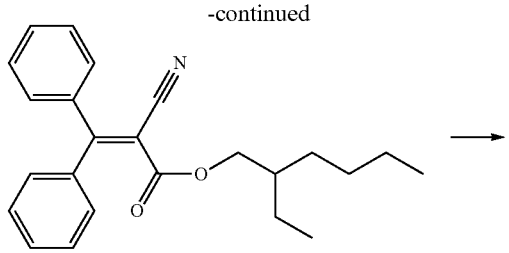

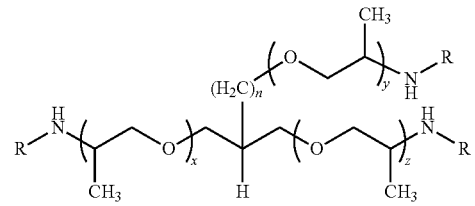

wherein R=

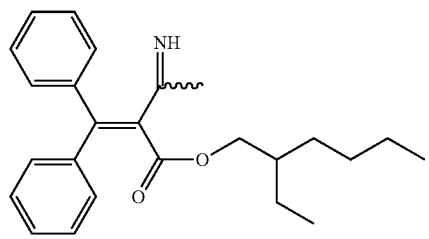

A triamine-terminated polypropylene glycol having an approximate molecular weight of 3000 g/mol (Jeffamine® T3000, Huntsman Corporation) (200 g) and octocrylene (Escalol® 597, International Specialty Products) (40 g) were charged into 0.5 L, four-necked resin kettle equipped with an anchor agitator, a thermocouple, a condenser, and a nitrogen surface purge adaptor.

The agitator was turned on to 200 rpm and the mixture was heated to 100° C. in XX minutes. During the entire reaction, nitrogen was purged through the reacting mixture. Once the temperature reached 180° C., the kettle was maintained isothermally for 46 hours. A vacuum was pulled for the final 8 hours to remove the excess volatile materials.

The synthesized polymer has a theoretical molar ratio of 1.8 effective amine units:1 UV absorber.

The invention has been described in detail with particular reference to preferred embodiments thereof, but it will be understood that variations and modifications can be effected within the spirit and scope of the invention.

What is claimed is:

1. An ultraviolet-absorbing compound derived from: at least one first reactant having a carbon-nitrogen triple bond, represented by the structure

where X represents the remaining structure of the first reactant, and at least one second reactant having amine functionality, represented by the structure

where Y represents the remaining structure of the second reactant, and R and R' are independently hydrogen or a non-hydrogen group, and the second reactant is selected from the group consisting of polyetheramines, polyethyleneimines or aminofunctional silicones, to result in the ultraviolet-absorbing compound having the structure

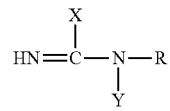

where a carbon of the carbon-nitrogen triple bond of the first reactant is covalently bound to a nitrogen of the amine functionality of the second reactant, wherein at least said first reactant or said second reactant is a UV absorber.

2. The ultraviolet-absorbing compound of claim 1 wherein said first reactant is said UV absorber.

3. The ultraviolet-absorbing compound of claim 2 wherein said first reactant has the structure:

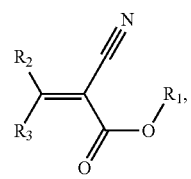

wherein $R_1$ and $R_3$ are independently selected from the group consisting of hydrogen, functionalized and unfunctionalized alkyl, cycloalkyl, alkenyl, and aryl groups, wherein any of the before mentioned groups may be present with or without heteroatoms; and $R_2$ is independently selected from the group consisting of hydrogen, halogen, functionalized and unfunctionalized alkyl, cycloalkyl, alkenyl, and aryl groups, wherein any of the before mentioned groups may be present with or without heteroatoms.

4. The ultraviolet-absorbing compound of claim 3 wherein said first reactant has the structure:

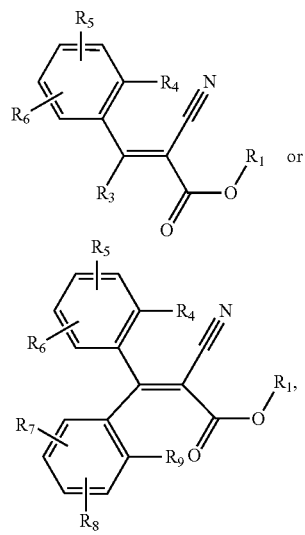

wherein one or both aryl groups may be substituted and wherein $R_1$ and $R_3$ are independently selected from the group consisting of hydrogen, functionalized and unfunctionalized alkyl, cycloalkyl, alkenyl, and aryl groups, wherein any of the before mentioned groups may be present with or without heteroatoms; and wherein $R_4$, $R_5$, $R_6$, $R_7$, $R_8$, and $R_9$ are independently selected from the group consisting of hydrogen, halogen, functionalized and unfunctionalized alkyl, cycloalkyl, alkenyl, and aryl groups, wherein any of the before mentioned groups may be present with or without heteroatoms.

5. The ultraviolet-absorbing compound of claim 4 wherein said first reactant has the structure:

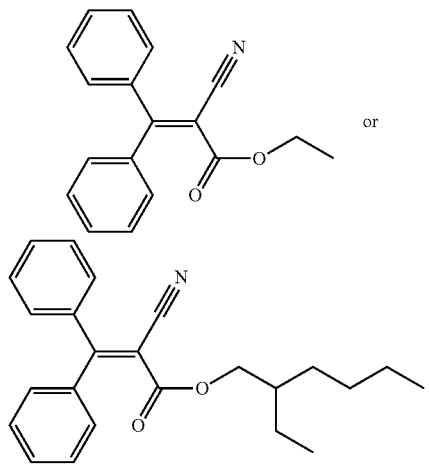

or

6. The ultraviolet-absorbing compound of claim 2 wherein said second reactant is selected from the group consisting of small molecules, monomers, macromolecules, biomolecules, and polymers.

7. The ultraviolet-absorbing compound of claim 6 wherein said second reactant is selected from the group consisting of: polyether monoamines, polyether diamines, polyether triamines, polyethyleneimines, polyethyleneimines having primary amine functionality, polyethyleneimines having secondary amine functionality, polyethyleneimines having primary and secondary amine functionality, aminofunctional silicones, isostearamidopropyl dimethylamine gluconate, propylene glycol amine-functional silicones, aminopropyl-terminated polydimethylsiloxanes, N-ethylamino-isobutyl-terminated-polydimethylsiloxanes, aminopropylmethylsiloxane-dimethylsiloxane copolymers, aminoethyl-aminopropylmethylsiloxane-dimethylsiloxane copolymers, aminoethyl-aminoisobutyl-methylsiloxane-dimethylsiloxane copolymers, and aminoethyl-aminopropylmethoxysiloxane-dimethylsiloxane copolymers, homopolymers of aminopolymers, copolymers of aminopolymers, terpolymers of aminopolymers alone or in combination thereof; or blends thereof.

8. The ultraviolet-absorbing compound of claim 1 that has a molecular weight from about 200 g/mol to about 5,000,000 g/mol.

9. The ultraviolet-absorbing compound of claim 1 that has from about 1% first reactant:99% second reactant to about 99% first reactant:1% second reactant (on effective weight basis).

10. A composition that comprises an ultraviolet-absorbing compound derived from: at least one first reactant having a carbon-nitrogen triple bond, represented by the structure

where X represents the remaining structure of the first reactant, and at least one second reactant having amine functionality, represented by the structure

R',R—N—Y where Y represents the remaining structure of the second reactant, and R and R' are independently hydrogen or a non-hydrogen group, and the second reactant is selected from the group consisting of polyetheramines, polyethyleneimines or aminofunctional silicones, to result in the ultraviolet-absorbing compound having the structure

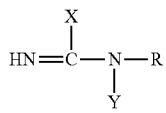

where a carbon of the carbon-nitrogen triple bond of the first reactant is covalently bound to a nitrogen of the amine functionality of the second reactant, wherein at least said first reactant or said second reactant is a UV absorber.

11. The composition of claim 10 which additionally comprises: an active, adhesive, anti-oxidant, binder, colorant, defoamer, dye, emollient, fragrance, humectant, UV absorber, lubricant, oil, pigment, preservative, propellant, surfactant, thickener, water, or wax.

12. The composition of claim 11 that is an adhesive, agriculture, cleaning/polishing, coating, containers, encapsulation, fragrances, imaging, hoses/tubing, household/industrial/institutional, medical, membrane, molded parts, oilfield, packaging, personal care, personal protective equipment, pharmaceutical, printing, veterinary, or wood-care composition.

13. The personal care composition of claim 12 that has the form of an aerosol, cream, gel, liquid, lotion, mist, mousse, paste, powder, roll-on, semi-solid, solid, or spray.

14. The personal care composition of claim 13 that is a sun-care composition.

15. The composition of claim 10 that further comprises at least one additional UV absorber.

16. The composition of claim 15 wherein said additional UV absorber is selected from the group consisting of: methoxydibenzoylmethane; octyl salicylate; pentyl dimethyl PABA; octyl dimethyl PABA; benzophenone-1; benzophenone-6; 2-(2H-benzotriazole-2-yl)-4,6-di-tert-pentylphenol; ethyl-2-cyano-3,3-diphenylacrylate; homomethyl salicylate; bis-ethylhexyloxyphenol methoxyphenyl triazine; methyl-(1,2,2,6,6-pentamethyl-4-piperidyl)-sebacate; 2-(2H-benzotriazole-2-yl)-4-methylphenol; diethylhexyl butamido triazone; amyl dimethyl PABA; 4,6-bis(octylthiomethyl)-o-cresol; CAS number 65447-77-0; red petroleum; ethylhexyl triazone; octocrylene; isoamyl-p-methoxycinnamate; drometrizole; titanium dioxide; 2,4-di-tert-butyl-6-(5-chloro-2H-benzotriazole-2-yl)-phenol; 2-hydroxy-4-octyloxybenzophenone; benzophenone-2; diisopropyl methylcinnamate; PEG-25 PABA; 2-(1,1-dimethylethyl)-6-[[3-(1,1-demethylethyl)-2-hydroxy-5-methylphenyl]methyl-4-methylphenyl acrylate; drometrizole trisiloxane; menthyl anthranilate; butyl methoxydibenzoylmethane; 2-ethoxyethyl p-methoxycinnamate; benzylidene camphor sulfonic acid; dimethoxyphenyl-[1-(3,4)]-4,4-dimethyl 1,3-pentanedione; zinc oxide; N,N'-hexane-1,6-diylbis[3-(3,5-di-tert-butyl-4-hydroxyphenylpropionamide)]; pentaerythritol tetrakis[3-(3,5-di-tert-butyl-4-hydroxyphenyl)propionate]; 2,6-di-tert-butyl-4-[4,6-bis(octylthio)-1,3,5-triazin-2-ylamino]phenol;

2-(2H-benzotriazole-2-yl)-4,6-bis(1-methyl-1-phenylethyl) phenol; trolamine salicylate; diethylanolamine p-methoxycinnamate; polysilicone-15; CAS number 152261-33-1; 4-methylbenzylidene camphor; bisoctrizole; N-phenyl-benzenamine; reaction products with 2,4,4-trimethylpentene; sulisobenzone; (2-ethylhexyl)-2-cyano-3,3-diphenylacrylate; digalloyl trioleate; polyacrylamido methylbenzylidene camphor; glyceryl ethylhexanoate dimethoxycinnamate; 1,3-bis-[(2'-cyano-3',3'-diphenylacryloyl)oxy]-2,2-bis-[(2'-cyano-bis-(2,2,6,6-tetramethyl-4-piperidyl)-sebacate; benzophenone-5; 1,3,5-tris(3,5-di-tert-butyl-4-hydroxybenzyl)-1,3,5-triazine-2,4,6(1H,3H,5H)-trione; hexamethylendiamine; benzophenone-8; ethyl-4-bis(hydroxypropyl)aminobenzoate; 6-tert-butyl-2-(5-chloro-2H-benzotriazole-2-yl)-4-methylphenol; p-aminobenzoic acid; 3,3',3",5,5',5"-hexa-tert-butyl-α-α'-α"-(mesitylene-2,4,6-triyl)tri-p-cresol; lawsone with dihydroxyacetone; benzophenone-9; benzophenone-4; ethylhexyl dimethoxy benzylidene dioxoimidazoline propionate; N,N'-bisformyl-N,N'-bis-(2,2,6,6-tetramethyl-4-piperidinyl)-; 3-benzylidene camphor; terephthalylidene dicamphor sulfonic acid; camphor benzalkonium methosulfate; bisdisulizole disodium; etocrylene; ferulic acid; 2-(2H-benzotriazole-2-yl)-4-(1,1,3,3-tetramethylbutyl)-phenol; 4,6-bis(dodecylthiomethyl)-o-cresol; β-2-glucopyranoxy propyl hydroxy benzophenone; phenylbenzimidazole sulfonic acid; benzophenone-3; diethylamine hydroxybenzoyl hexylbenzoate; 3',3'-diphenylacryloyl)oxy]methyl}-propane; ethylhexyl p-methoxycinnamate, and blends thereof.

* * * * *